(12) United States Patent
Fu

(10) Patent No.: US 6,861,420 B2
(45) Date of Patent: Mar. 1, 2005

(54) N-SUBSTITUTED 1,2,4,5-TETRAHYDRO-1H-BENZO[D]AZEPINE COMPOUNDS

(75) Inventor: Jian-Min Fu, Kalamazoo, MI (US)

(73) Assignee: Pharmacia & Upjohn Company, Kalamazoo, MI (US)

( * ) Notice: Subject to any disclaimer, the term of this patent is extended or adjusted under 35 U.S.C. 154(b) by 0 days.

(21) Appl. No.: 10/305,408

(22) Filed: Nov. 26, 2002

(65) Prior Publication Data

US 2003/0149024 A1 Aug. 7, 2003

Related U.S. Application Data

(60) Provisional application No. 60/334,012, filed on Nov. 28, 2001.

(51) Int. Cl.⁷ ............... C07D 223/16; A61K 31/55; A61P 25/18; A61P 25/22; A61P 25/24
(52) U.S. Cl. ............... 514/217.01; 540/594
(58) Field of Search ............... 540/594; 514/217.01

(56) References Cited

U.S. PATENT DOCUMENTS 5,132,311 A * 7/1992 Liang ............... 514/307
2002/0019389 A1 * 2/2002 Kim et al. ............... 514/213.01

FOREIGN PATENT DOCUMENTS

| WO | WO 97/48699 | 12/1997 |
| WO | WO 97/48700 | 12/1997 |
| WO | WO 01/95856 | * 12/2001 |

OTHER PUBLICATIONS

Robichaud et al. (Annual reports in Medicinal Chemistry 35, Chapter 2) 2000.*

* cited by examiner

*Primary Examiner*—Bruck Kifle
(74) *Attorney, Agent, or Firm*—Flynn, Thiel, Boutell & Tanis, P.C.

(57) ABSTRACT

The present invention provides compounds of Formula I:

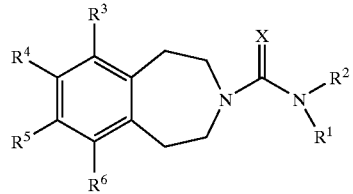

Formula I wherein X, $R^1$, $R^2$, $R^3$, $R^4$, $R^5$, and $R^6$ have any of the values defined in the specification, as well as pharmaceutical compositions comprising the compounds. The invention also provides therapeutic methods as well as processes and intermediates useful for preparing compounds of Formula I.

59 Claims, No Drawings

N-SUBSTITUTED 1,2,4,5-TETRAHYDRO-1H-BENZO[D]AZEPINE COMPOUNDS

CROSS-REFERENCE TO RELATED APPLICATION

This application claims the benefit of U.S. provisional application Ser. No. 60/334,012, filed Nov. 28, 2001, under 35 U.S.C. 119(e)(i), which is incorporated herein by reference.

FIELD OF THE INVENTION

The present invention provides urea compounds of Formula I as described herein below. These compounds and pharmaceutically acceptable salts thereof, are serotonin receptor ligands useful for treating a variety of diseases and conditions related to 5-HT receptor activity.

BACKGROUND OF THE INVENTION

Serotonin has been implicated in a number of diseases and conditions that originate in the central nervous system. These include diseases and conditions related to sleeping, eating, perceiving pain, controlling body temperature, controlling blood pressure, depression, anxiety, schizophrenia, and other bodily states. R. W. Fuller, Biology of Serotonergic Transmission, ed. Neville V. Osborne, John Wiley and Sons (1982), p 221; D. J. Boullin, Serotonin in Mental Abnormalities 1, John Wiley and Sons (1978), p. 316; J. Barchas, et al., Serotonin and Behavior, Academic Press, New York, N.Y. (1973); Barnes, N. M.; A Review Of Central 5-HT Receptors And Their Function, *Neuropharmacology*, 38, (1999), 1083–1152. Serotonin also plays an important role in peripheral systems, such as the gastrointestinal system, where it has been found to mediate a variety of contractile, secretory, and electrophysiologic effects.

As a result of the broad distribution of serotonin within the body, there is a tremendous interest in drugs that affect serotonergic systems. In particular, receptor-specific agonists and antagonists are of interest for the treatment of a wide range of disorders, including anxiety, depression, hypertension, migraine, obesity, compulsive disorders, schizophrenia, autism, neurodegenerative disorders, for example, Alzheimer's disease, Parkinsonism, and Huntington's chorea, and chemotherapy-induced vomiting. M. D. Gershon, et al., The Peripheral Actions of 5-Hydroxytryptamine, 246 (1989); P. R. Saxena, et al., *Journal of Cardiovascular Pharmacology*, 15: Supplement 7 (1990).

The major classes of serotonin receptors ($5-HT_{1-7}$) contain fourteen to eighteen separate receptors that have been formally classified. See Glennon, et al., *Neuroscience and Behavioral Reviews*, 1990, 14, 35; and D. Hoyer, et al. *Pharmacol. Rev.* 1994, 46, 157–203. Recently discovered information regarding subtype identity, distribution, structure, and function suggests that it is possible to identify novel, subtype specific agents, having improved therapeutic profiles, for example, fewer side effects.

For example, the $5-HT_2$ family of receptors is comprised of $5-HT_{2A}$, $5-HT_{2B}$, and $5-HT_{2C}$ subtypes, which have been grouped together on the basis of primary structure, secondary messenger system, and operational profile. All three subtypes are G-protein coupled, activate phospholipase C as a principal transduction mechanism, and contain a seven-transmembrane domain structure. There are distinct differences in the distribution of the three $5-HT_2$ subtypes. The $5-HT_{2B}$ and $5-HT_{2A}$ receptors are widely distributed in the periphery, while the $5-HT_{2C}$ receptor has been found only in the central nervous system, being highly expressed in many regions of the human brain. See G. Baxter, et al., *Trends in Pharmacol. Sci.*, 1995, 16, 105–110.

Subtype $5-HT_{2A}$ has been associated with effects including vasoconstriction, platelet aggregation, and bronchoconstriction, while subtype $5-HT_{2C}$ has been associated with diseases that include depression, anxiety, obsessive compulsive disorder, panic disorders, phobias, psychiatric syndromes, and obesity. Very little is known about the pharmacologic role of the $5-HT_{2B}$ receptor. See F. Jenck, et al., *Exp. Opin. Invest. Drugs*, 1998, 7, 1587–1599; M. Bos, et al., *J. Med. Chem.*, 1997, 40, 2762–2769; J. R. Martin, et al., *The Journal of Pharmacology and Experimental Therapeutics*, 1998, 286, 913–924; S. M. Bromidge, et al., *J. Med. Chem.*, 1998, 41 1598–1612; G. A. Kennett, *IDrugs*, 1998, 1, 456–470; and A. Dekeyne, et al., *Neuropharmacology*, 1999, 38, 415–423; Isaac, M., *Drugs of the Future*, 2001, 26, 383–393.

INFORMATION DISCLOSURE

International Patent Application Publication Number WO 97/48699 discloses compounds of the general formula

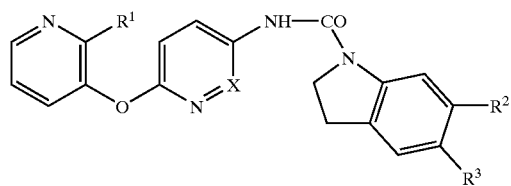

useful in the treatment of CNS disorders such as anxiety.

International Patent Application Publication Number WO 97/48700 discloses compounds of the general formula

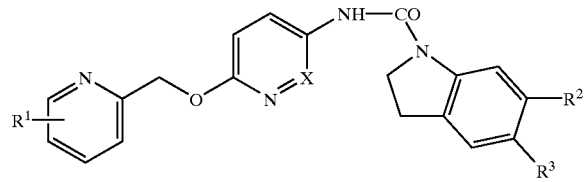

useful in the treatment of CNS disorders such as anxiety.

In spite of the above reports, there is currently a need for pharmaceutical agents that are useful to treat diseases and conditions associated with 5-HT receptors.

SUMMARY OF THE INVENTION

In accordance with the present invention, novel compounds which demonstrate useful biological activity, and particularly activity as 5-HT receptor ligands, are provided.

Thus, the present invention provides N-substituted 1,2,4,5-tetrahydro-1H-benzo[d]azepine compounds of formula I:

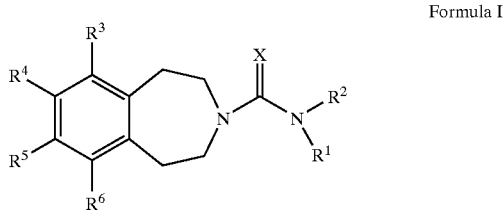

Formula I wherein
X is O, S, or N—$R_b$;
$R^1$ is —Y-Q-Z;
Y is heterocycle, substituted heterocycle, heteroaryl, or substituted heteroaryl,
Q is absent or is —O—, —S(O)$_m$—, —NR$_a$—, or alkylene;
Z is aryl, substituted aryl, heterocycle, substituted heterocycle, heteroaryl, substituted heteroaryl, or absent provided that Q is also absent;
$R^2$ is H, $C_{1-8}$alkyl, or aryl($C_{1-8}$alkylene-);
$R^3$, $R^4$, $R^5$, and $R^6$ are each independently H, hydroxy, nitro, halo, cyano, $N_3$, amidine, guanidine, thioguanidine, cyanoguanidine, $C_{1-8}$alkyl, $C_{1-8}$haloalkyl, $C_{1-8}$alkoxy, $C_{1-8}$haloalkoxy, $C_{3-8}$cycloalkyl, aryl, heteroaryl, substituted heteroaryl, —S(O)NR$_c$R$_d$, —S(O)$_2$NR$_c$R$_d$, —NR$_c$R$_d$, —S(O)$_m$R$_a$, —C(=O)NR$_c$R$_d$, —C(=S)NR$_c$R$_d$, —N(R$_a$)—S(O)R$_a$, or —N(R$_a$)—S(O)$_2$R$_a$;
each R$_a$ is independently H, $C_{1-8}$alkyl, $C_{1-8}$alkanoyl, $C_{1-8}$alkoxycarbonyl, aryl, aryl($C_{1-8}$alkylene-), heteroaryl, heteroaryl($C_{1-8}$alkylene-), heterocycle, or heterocycle($C_{1-8}$alkylene-);
R$_b$ is hydrogen, ($C_{1-8}$alkyl, $C_{1-8}$alkanoyl, $C_{1-8}$alkoxycarbonyl, cyano, aryl, aryl($C_{1-8}$alkylene-), heteroaryl, heteroaryl($C_{1-8}$alkylene-), heterocycle, or heterocycle($C_{1-8}$alkylene-);
each of R$_c$ and R$_d$ is independently H, $C_{1-8}$alkyl, $C_{1-8}$alkanoyl, $C_{1-8}$alkoxycarbonyl, aryl, aryl($C_{1-8}$alkylene-), heteroaryl, heteroaryl($C_{1-8}$alkylene-), heterocycle, or heterocycle($C_{1-8}$alkylene-); or R$_c$ and R$_d$ together with the nitrogen to which they are attached form azepino, piperazino, pyrrolidino, piperidino, morpholino, or thiomorpholino ring;
each m is independently 0, 1, or 2;
or a pharmaceutically acceptable salt thereof.
In another aspect, the invention also provides:
a pharmaceutical composition comprising a compound of Formula I, or a pharmaceutically acceptable salt thereof, and a pharmaceutically acceptable excipient, the composition preferably comprises a therapeutically effective amount of the compound or salt;
a method for treating a disease or condition in a mammal in need thereof, for example, a human, wherein a 5-HT receptor is implicated and modulation of a 5-HT function is desired comprising administering a therapeutically effective amount of a compound of Formula I, or a pharmaceutically acceptable salt thereof to the mammal;
a method for treating a disease or disorder of the central nervous system in a mammal in need thereof comprising administering a therapeutically effective amount of a compound of Formula I, or a pharmaceutically acceptable salt thereof to the mammal;
a compound of Formula I or a pharmaceutically acceptable salt thereof for use in medical diagnosis or therapy, for example, the treatment or prevention of 5-HT related disease such as anxiety, obesity, depression, or a stress related disease;

the use of a compound of Formula I, or a pharmaceutically acceptable salt thereof to prepare a medicament useful for treating or preventing a disease or disorder of the central nervous system in a mammal in need thereof; and
a method for modulating 5-HT receptor function, comprising administering an effective modulatory amount of a compound of Formula I, or a pharmaceutically acceptable salt thereof.
The invention also provides synthetic intermediates and processes disclosed herein that are useful for preparing compounds of Formula I.
Compounds of Formula I are 5-HT ligands. Thus, radiolabeled compounds of Formula I are useful as imaging agents and biomarker for medical therapy and diagnosis. Such radiolabeled compounds are also useful as pharmacological tools for studying 5-HT function and activity. Accordingly, the invention also provides a radiolabeled compound of Formula I, or a salt thereof.
Compounds of Formula I can be labeled using techniques which are well known in the art. For example, a radioisotope can be incorporated into the compound or appended to the compound of Formula I using techniques well known in the art. For example, see Arthur Murry III, D. Lloyd Williams; *Organic Synthesis with Isotopes*, vol. I and II, Interscience Publishers Inc., N.Y. (1958) and Melvin Calvin et al. *Isotopic Carbon* John Wiley and Sons Inc., N.Y. (1949). Any radioisotope capable of being detected can be employed as a label. For example, suitable radioisotopes include: carbon-11, fluorine-18, fluorine-19, iodine-123 and iodine-125. Preferably, a compound of formula I may be labeled by appending one or more radioisotopes of a halogen (e.g. iodine-123) to an aromatic ring, or by alkylating a nitrogen of a compound of Formula I with a group comprising a phenyl group bearing a radioisotope.
The invention also provides a radiolabeled compound of Formula I for use in medical diagnosis or therapy, as well as the use of a radiolabeled compound of Formula I to prepare a medicament useful for medical diagnosis or therapy.
Further aspects and embodiments of the invention may become apparent to those skilled in the art from a review of the following detailed description, taken in conjunction with the examples and the appended claims. While the invention is susceptible of embodiments in various forms, described hereafter are specific embodiments of the invention with the understanding that the present disclosure is intended as illustrative, and is not intended to limit the invention to the specific embodiments described herein.

DETAILED DESCRIPTION OF THE INVENTION

The compounds of the invention are useful for treating diseases or disorders of the central nervous system. Specific diseases or disorders of the central nervous system for which a compound of Formula I may have activity include, but are not limited to: obesity, depression, schizophrenia, schizophreniform disorder, schizoaffective disorder, delusional disorder, a stress related disease, for example, general anxiety disorder, panic disorder, a phobia, obsessive compulsive disorder, post-traumatic-stress syndrome, immune system depression, a stress induced problem with the urinary, gastrointestinal or cardiovascular system, for example, stress incontinence, neurodegenerative disorders, autism, chemotherapy-induced vomiting, hypertension, migraine, headaches, cluster headaches, sexual dysfunction in a mammal, for example, a human, addictive disorder and withdrawal syndrome, an adjustment disorder, an age-associated learning and mental disorder, anorexia nervosa, apathy, an attention-deficit disorder due to general medical conditions, attention-deficit hyperactivity disorder, behavioral disturbance, including agitation in conditions associated with diminished cognition, for example, dementia, mental retardation or delirium; bipolar disorder, bulimia nervosa, chronic fatigue syndrome, conduct disorder, cyclothymic disorder, dysthymic disorder, fibromyalgia and other somatoform disorders, an inhalation disorder, an intoxication disorder, movement disorder, for example, Huntington's disease or Tardive Dyskinesia, oppositional defiant disorder, peripheral neuropathy, post-traumatic stress disorder, premenstrual dysphoric disorder, a psychotic disorder (brief and long duration disorders, psychotic disorder due to medical condition, psychotic disorder NOS), mood disorder (major depressive or bipolar disorder with psychotic features) seasonal affective disorder, a sleep disorder, a specific development disorder, agitation disorder, selective serotonin reuptake inhibition (SSRI) "poop out" syndrome or a Tic disorder, for example, Tourette's syndrome. Treatment includes prophylactic treatment.

The following definitions are used, unless otherwise described: halo is fluoro, chloro, bromo, or iodo. Alkyl, alkoxy, etc. denote both straight and branched groups; but reference to an individual radical such as "propyl" embraces only the straight chain radical, a branched chain isomer such as "isopropyl" being specifically referred to. The term "alkylene" refers to a divalent straight or branched hydrocarbon chain (e.g. ethylene —$CH_2CH_2$—). The term "aryl$C_{1-8}$alkylene-" means a substituent consisting of an aryl group attached to an alkylene moiety, with the alkylene moiety providing the point of attachment of the substituent group. The term "aryl($C_{1-8}$alkylene-)" for example includes benzyl, phenethyl, naphthylmethyl and the like. The term "substituted aryl($C_{1-8}$alkylene-)" means a substituent consisting of a substituted aryl group attached to an alkylene moiety, with the alkylene moiety providing the point of attachment of the substituent group.

The term "heteroaryl($C_{1-8}$alkylene-)" means a substituent consisting of a heteroaryl group attached to an alkylene moiety, with the alkylene moiety providing the point of attachment of the substituent group.

The term "substituted heteroaryl($C_{1-8}$alkylene-)" means a substituent consisting of an substituted heteroaryl group attached to an alkylene moiety, with the alkylene moiety providing the point of attachment of the substituent group.

The term "heterocycle($C_{1-8}$alkylene-)" means a substituent consisting of a heterocycle group attached to an alkylene moiety, with the alkylene moiety providing the point of attachment of the substituent group.

The term "substituted heterocycle($C_{1-8}$alkylene-)" means a substituent consisting of an substituted heterocycle group attached to an alkylene moiety, with the alkylene moiety providing the point of attachment of the substituent group.

"Aryl" denotes a phenyl radical or an ortho-fused bicyclic carbocyclic radical having about nine to ten ring atoms in which at least one ring is aromatic. Non-limiting examples of aryl include phenyl, naphthyl, and indenyl.

"Heteroaryl" denotes a radical of a monocyclic aromatic ring containing five or six ring atoms consisting of carbon and 1, 2, 3, or 4 heteroatoms each selected from the group consisting of non-peroxide oxygen, sulfur, and N(W) wherein W is absent or is H, O, $C_{1-4}$alkyl, phenyl or benzyl, as well as a radical of an ortho-fused bicyclic heterocycle of about eight to ten ring atoms derived therefrom, particularly a benz-derivative or one derived by fusing a propylene, trimethylene, or tetramethylene diradical thereto. Non-limiting examples of heteroaryl groups include, but are not limited to, 2H-pyrrolyl, 3H-indolyl, 4H-quinolizinyl, 4H-carbazolyl, acridinyl, benzo[b]thienyl, benzothiazolyl, β-carbolinyl, carbazolyl, chromenyl, cinnaolinyl, furazanyl, furyl, imidazolyl, imidizolyl, indazolyl, indolisinyl, indolyl, isobenzofuranyl, isoindolyl, isoquinolyl, isothiazolyl, isothiazolyl, isoxazolyl, isoxazolyl, naphthyridinyl, naptho [2,3-b], oxazolyl, perimidinyl, phenanthridinyl, phenanthrolinyl, phenarsazinyl, phenazinyl, phenothiazinyl, phenoxathiinyl, phenoxazinyl, phthalazinyl, pteridinyl, purinyl, pyranyl, pyrazinyl, pyrazolyl, pyridazinyl, pyridinyl, pyrimidinyl, pyrimidinyl, pyrrolyl, quinazolinyl, quinolyl, quinoxalinyl, thiadiazolyl, thianthrenyl, thiazolyl, thienyl, triazolyl, xanthenyl, and the like. The heteroaryl attaches not only at any carbon atom, but also at any heteroatom that can form a stable compound.

"Heterocycle" includes monocyclic, polycyclic, and bridged ring systems, which can be saturated or partially unsaturated, containing one or more non-aromatic rings, such as 2, 3, or 4, and containing at least one nitrogen, oxygen, or sulfur atom in any of the non-aromatic rings. Non-limiting examples of heterocyclic groups include, but are not limited to, monocyclic, bicyclic, or tricyclic groups which groups contain one or more heteroatoms and from about 3 to about 20 total ring atoms. The term "heterocycle" also includes such ring systems that include one to three benzo rings fused thereto. Non-limiting examples of heterocycle include, for example, 1,3-dioxolanyl, 1,4-dioxanyl, 1,4-dithianyl, 2H-pyranyl, 2-pyrazolinyl, 4H-pyranyl, chromanyl, imidazolidinyl, imidazolinyl, indolinyl, isochromanyl, isoindolinyl, morpholine, piperazinyl, piperidine, piperidyl, pyrazolidine, pyrazolidinyl, pyrazolinyl, pyrrolidinyl, pyrrolinyl, quinuclidinyl, and thiomorpholinyl.

"Substituted aryl" includes an aryl group as described herein which is substituted with one or more (e.g. 1, 2, 3, or 4) substituents independently selected from nitro, $C_{1-8}$alkyl, $C_{1-8}$alkoxy, cyano, $N_3$, $OCF_3$, $CF_3$, halo, hydroxy, —$S(O)_{0-2}C_{1-8}$alkyl, $C_{1-8}$alkanoyl, $C_{1-8}$alkanoyloxy, —$NR_eR_f$, —$C(=O)NR_eR_f$, —$C(=S)NR_eR_f$, and —$SO_2NR_eR_f$, wherein $R_e$ and $R_f$ are each independently hydrogen, $C_{1-8}$alkyl, $C_{1-8}$alkanoyl, $C_{1-8}$alkoxycarbonyl, aryl, aryl($C_{1-8}$alkylene-), heteroaryl, heteroaryl($C_{1-8}$alkylene-), heterocycle, or heterocycle($C_{1-8}$alkylene-), or $R_e$ and $R_f$ together with the nitrogen to which they are attached form a pyrrolidino, piperidino, morpholino, or thiomorpholino ring.

"Substituted heteroaryl" includes a heteroaryl group as described herein which is substituted with one or more (e.g. 1, 2, 3, or 4) substituents independently selected from nitro, $N_3$, $C_{1-8}$alkyl, $C_{1-8}$alkoxy, cyano, $OCF_3$, $CF_3$, halo, hydroxy, —$S(O)_{0-2}C_{1-8}$alkyl, $C_{1-8}$alkanoyl, $C_{1-8}$alkanoyloxy, —$NR_eR_f$, —$C(=O)NR_eR_f$, —$C(=S)NR_eR_f$, and —$SO_2NR_cR_d$, wherein $R_e$ and $R_f$ are each independently hydrogen, $C_{1-8}$alkyl, $C_{1-8}$alkanoyl, $C_{1-8}$alkoxycarbonyl, aryl, aryl($C_{1-8}$alkylene-), heteroaryl, heteroaryl($C_{1-8}$alkylene), heterocycle, or heterocycle($C_{1-8}$alkylene), or $R_e$ and $R_f$ together with the nitrogen to which they are attached form a pyrrolidino, piperidino, morpholino, or thiomorpholino ring.

"Substituted heterocycle" includes a heterocycle as described herein which is substituted with one or more (e.g. 1, 2, 3, or 4) substituents independently selected from nitro, $C_{1-8}$alkyl, $C_{1-8}$alkoxy, cyano, $N_3$, $OCF_3$, $CF_3$, halo, hydroxy, —$S(O)_{0-2}C_{1-8}$alkyl, $C_{1-8}$alkanoyl, $C_{1-8}$alkanoyloxy, —$NR_eR_f$, —$C(=O)NR_eR_f$, —$C(=S)NR_eR_f$, —$SO_2NR_cR_d$, and oxo (=O), wherein $R_e$ and $R_f$ are each independently hydrogen, $C_{1-8}$alkyl, $C_{1-8}$alkanoyl, $C_{1-8}$alkoxycarbonyl, aryl, aryl($C_{1-8}$alkylene-), heteroaryl, heteroaryl($C_{1-8}$alkylene-), heterocycle, or heterocycle ($C_{1-8}$alkylene-), or $R_e$ and $R_f$ together with the nitrogen to which they are attached form a pyrrolidino, piperidino, morpholino, or thiomorpholino ring.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, tautomeric, or stereoisomeric form, or mixture thereof, of a compound of the invention, which possesses the useful properties described herein, it being well known in the art how to prepare optically active forms, for example, by resolution of the racemic form by recrystallization techniques, by synthesis from optically-active starting materials, by chiral synthesis, or by chromatographic separation using a chiral stationary phase, and how to determine 5-HT activity using the standard tests which are well known in the art.

The carbon atom content of various hydrocarbon-containing moieties is indicated by a prefix designating the minimum and maximum number of carbon atoms in the moiety, that is, the prefix $C_{i-j}$ indicates a moiety of the integer "i" to the integer "j" carbon atoms, inclusive. Thus, for example, $C_{1-8}$alkyl refers to alkyl of one to eight carbon atoms, inclusive.

The compounds of the present invention are generally named according to the IUPAC or CAS nomenclature system. Abbreviations which are well known to one of ordinary skill in the art may be used, for example, "Ph" for phenyl, "Me" for methyl, "Et" for ethyl, "h" for hour or hours and "rt" for room temperature (20–25° C.).

To the extent that any numerical range is recited in connection with any aspect of the inventive compounds, for example, dosages, treatment regimens, and the like, the range expressly includes all numerals, integer and fractional, falling within the range.

Specific and preferred values listed below for radicals, substituents, and ranges, are for illustration only; they do not exclude other defined values or other values within defined ranges.

Specifically, $C_{1-8}$ alkyl can be methyl, ethyl, propyl, isopropyl, butyl, iso-butyl, sec-butyl, pentyl, 3-pentyl, hexyl, heptyl or octyl; $C_{1-8}$alkylene can be methylene, 1,2-ethanediyl, 1,3-propanediyl, 1,2-isopropanediyl, 1,4-butanediyl, 1,2-butanediyl, 1,3-iso-butanediyl, 1,2-sec-butanediyl, 1,5-pentanediyl, 1,6-hexanediyl, 1,7-heptanediyl, or 1,8-octanediyl; $C_{1-8}$alkoxy can be methoxy, ethoxy, propoxy, isopropoxy, butoxy, iso-butoxy, sec-butoxy, pentoxy, 3-pentoxy, hexyloxy, heptyloxy, or octyloxy; $C_{1-8}$alkanoyl can be acetyl, propanoyl, butanoyl, pentanoyl, 4-methylpentanoyl, hexanoyl, or heptanoyl; $C_{1-8}$alkoxycarbonyl can be methoxycarbonyl, ethoxycarbonyl, propoxycarbonyl, isopropoxycarbonyl, butoxycarbonyl, pentoxycarbonyl, hexyloxycarbonyl, heptyloxycarbonyl, or octyloxycarbonyl; $C_{1-8}$haloalkyl can be methyl, ethyl, propyl, isopropyl, butyl, iso-butyl, sec-butyl, pentyl, 3-pentyl, hexyl, heptyl or octyl, with one or more halogen atom substituents; $C_{1-8}$haloalkoxy can be methoxy, ethoxy, propoxy, isopropoxy, butoxy, iso-butoxy, sec-butoxy, pentoxy, 3-pentoxy, hexyloxy, heptyloxy, or octyloxy, with one or more halogen atom substituents; $C_{3-8}$cycloalkyl can be cyclopropyl, cyclobutyl, cyclopentyl, cyclohexyl, cycloheptyl or cyclooctyl; and $C_{1-8}$alkanoyloxy can be acetyloxy, propanoyloxy, butanoyloxy, isobutanoyloxy, pentanoyloxy, hexanoyloxy, heptanoyloxy, or octanoyloxy.

A specific value for X is O.

Another specific value for X is S.

Another specific value for X is N—CN.

Another specific value for X is N—$R_b$.

A specific value for Y is heteroaryl or substituted heteroaryl.

Another specific value for Y is pyridin-3-yl or 2-halo-pyridin-3-yl.

Another specific value for Y is heterocycle or substituted heterocycle.

Another specific value for Y is piperidin-3-yl or quinuclidin-3-yl.

A more specific value for Y is pyridin-3-yl.

A specific value for $R^1$ is 6-(2-methyl-pyridin-3-yloxy)-pyridin-3-yl and X is O.

A specific value for $R^2$ is H.

Another specific value for $R^2$ is $C_{1-8}$alkyl.

Another specific value for $R^2$ is aryl($C_{1-8}$alkylene-).

A specific value for $R^3$ is H.

Another specific value for $R^3$ is halo.

Another specific value for $R^3$ is alkyl.

A specific value for $R^4$ is H.

Another specific value for $R^4$ is substituted heteroaryl.

Another specific value for $R^4$ is 2,5-dimethyl pyrrol-1-yl.

Another specific value for $R^4$ is halo.

Another specific value for $R^4$ is alkyl.

A specific value for $R^5$ is H.

A specific value for $R^6$ is H.

Another specific value for $R^6$ is halo.

Another specific value for $R^6$ is alkyl.

A specific group of compounds of formula I are compounds wherein Y is heterocycle or heteroaryl, each substituted with hydroxy and Q and Z are both absent.

Another specific group of compounds of Formula I are compounds wherein Q is —O— and Z is substituted heteroaryl.

Another specific group of compounds of Formula I are compounds wherein Q is —O— and Z is substituted aryl.

Another specific group of compounds of Formula I are compounds wherein Q is —O— and Z is 2-methyl-pyridin-3-yl.

Another specific group of compounds of Formula I are compounds wherein Q is —O— and Z is alkoxy substituted phenyl.

Another specific group of compounds of Formula I are compounds wherein Q is —O— and Z is 4-halo substituted phenyl.

Another specific group of compounds of Formula I are compounds wherein Q is —O— and Z is a halo and alkyl substituted phenyl.

Another specific group of compounds of Formula I are compounds wherein Q is —O— and Z is a halo and dialkyl substituted phenyl.

Another specific group of compounds of Formula I are compounds wherein Q is —O—, and Z is a dihalo substituted phenyl.

A specific compound of Formula I is of Formula II:

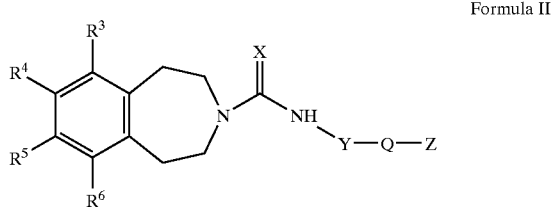

Formula II wherein $R^3$–$R^6$, Q, X, Y, and Z have any of the values, specific values or preferred values described herein.

A specific compound of Formula II is a compound wherein Y is heterocycle or substituted heterocycle; and Q and Z are absent.

A specific compound of Formula II is a compound wherein Y is heteroaryl or substituted heteroaryl; and Q and Z are absent.

A specific compound of Formula I is of Formula III:

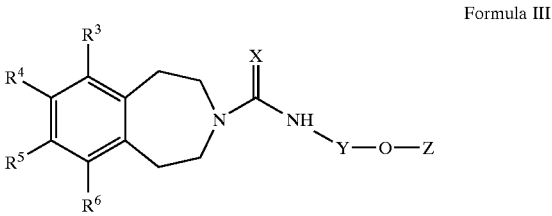

Formula III wherein $R^3$–$R^6$, X, Y, and Z have any of the values, specific values or preferred values described herein.

A specific compound of Formula III is a compound wherein Y is heterocycle or substituted heterocycle; and Z is aryl, substituted aryl, heterocycle, substituted heterocycle, heteroaryl, or substituted heteroaryl.

A specific compound of Formula III is a compound wherein Y is heteroaryl or substituted heteroaryl; and Z is aryl, substituted aryl, heterocycle, substituted heterocycle, heteroaryl, or substituted heteroaryl.

A preferred compound of formula I is any one or more of the following: N-{6-[(2-methylpyridin-3-1)oxy]pyridin-3-yl}-1,2,4,5-tetrahydro-3H-3-benzazepine-3-carboxamide; 7-(2,5-dimethyl-1H-pyrrol-1-yl)-N-{6-[(2-methylpyridin-3-yl)oxy]pyridin-3-yl}-1,2,4,5-tetrahydro-3H-3-benzazepine-3-carboxamide; 7-chloro-N-{6-[(2-methylpyridin-3-yl)oxy]pyridin-3-yl}-1,2,4,5-tetrahydro-3H-3-benzazepine-3-carboxamide; 7-chloro-8-methyl-N-{6-[(2-methylpyridin-3-yl)oxy]pyridin-3-yl}-1,2,4,5-tetrahydro-3H-3-benzazepine-3-carboxamide; 1,2,4,5-Tetrahydro-benzo[d]azepine-3-carboxylic acid pyridin-3-ylamide; N-[2-chloropyridin-3-yl]-1,2,4,5-tetrahydro-3H-3-benzazepine-3-carboxamide; N-(6-chloropyridin-3-yl)-1,2,4,5-tetrahydro-3H-3-benzazepine-3-carboxamide; N-(6-Methoxypyridin-3-yl)-1,2,4,5-tetrahydro-3H-3-benzazepine-3-carboxamide; N-[6-(4-methoxyphenoxy)pyridin-3-yl]-1,2,4,5-tetrahydro-3H-3-benzazepine-3-carboxamide; N-[6-(4-chlorophenoxy)pyridin-3-yl]-1,2,4,5-tetrahydro-3H-3-benzazepine-3-carboxamide; N-[6-(2-fluorophenoxy)pyridin-3-yl]-1,2,4,5-tetrahydro-3H-3-benzazepine-3-carboxamide; N-[6-(2-isopropoxyphenoxy)pyridin-3-yl]-1,2,4,5-tetrahydro-3H-3-benzazepine-3-carboxamide; N-[6-(2-methyl-4-chlorophenoxy)pyridin-3-yl]-1,2,4,5-tetrahydro-3H-3-benzazepine-3-carboxamide; N-[6-(3-methyl-4-chlorophenoxy)pyridin-3-yl]-1,2,4,5-tetrahydro-3H-3-benzazepine-3-carboxamide; N-[6-(2,4-dichlorophenoxy)pyridin-3-yl]-1,2,4,5-tetrahydro-3H-3-benzazepine-3-carboxamide; N-[6-(4-chloro-3,5-dimethylphenoxy)pyridin-3-yl]-1,2,4,5-tetrahydro-3H-3-benzazepine-3-carboxamide; N-Piperidin-3-yl-1,2,4,5-tetrahydro-3H-3-benzazepine-3-carboxamide; N-(1-azabicyclo[2.2.2]oct-3-yl)-1,2,4,5-tetrahydro-3H-3-benzazepine-3-carboxamide; N-[(3R)-1-azabicyclo[2.2.2]oct-3-yl]-1,2,4,5-tetrahydro-3H-3-benzazepine-3-carboxamide; or N-[(3S)-1-azabicyclo[2.2.2]oct-3-yl]-1,2,4,5-tetrahydro-3H-3-benzazepine-3-carboxamide.

Specifically, the invention also provides a method for treating anxiety, obesity, depression, schizophrenia, or a stress related disease such as a general anxiety disorder, panic disorder, a phobia, obsessive compulsive disorder, post-traumatic-stress syndrome, immune system depression, a stress induced problem with the gastrointestinal or cardiovascular system, or sexual dysfunction in a mammal, comprising administering a therapeutically effective amount of a compound of Formula I, II, III, or a pharmaceutically acceptable salt thereof to the mammal.

Specifically, the invention also provides a method of treating anxiety, obesity, depression, or a stress related disease, comprising administering to a mammal, for example a human, in need of such treatment, a therapeutically effective amount of a compound of Formula I, II, III, or a pharmaceutically acceptable salt thereof.

Specifically, the invention also provides the use of a compound of Formula I, II, III, or a pharmaceutically acceptable salt thereof to prepare a medicament for treating anxiety, obesity, depression, schizophrenia, a stress related disease, such as a general anxiety disorder, panic disorder, a phobia, obsessive compulsive disorder, post-traumatic-stress syndrome, immune system depression, a stress induced problem with the gastrointestinal or cardiovascular system, or sexual dysfunction in a mammal, for example a human.

Specifically, the invention also provides the use of a compound of Formula I, II, III, or a pharmaceutically acceptable salt thereof to prepare a medicament for treating anxiety, obesity, depression, or a stress related disease in a mammal, for example a human.

The invention also provides processes and intermediates useful for preparing compounds of Formula I, II, III, or pharmaceutical acceptable salt thereof. For example, an intermediate useful for preparing a compound of Formula I is a corresponding compound of Formula I wherein $R^2$ is a suitable amine protecting group. Thus, the invention provides a compound of Formula I, II, III, or a pharmaceutically acceptable salt thereof, wherein $R^2$ is a suitable amine protecting group.

Suitable amine protecting groups, as well as methods for their preparation and removal are well known in the art, for example, see Greene, T. W.; Wutz, P. G. M. "Protecting Groups In Organic Synthesis" third edition, 1999, New York, John Wiley & sons, Inc. Preferred protecting groups include benzyloxycarbonyl (CBZ) and benzoyl.

The invention also provides novel intermediate compounds that are useful in preparing compounds of Formula I, II, III, or pharmaceutically acceptable salts thereof, for example, the formulas as shown in preparative schemes below.

The invention also provides intermediate salts that are useful for preparing or purifying compounds of Formula I, II, III, or a pharmaceutically acceptable salt thereof. Suitable methods for preparing pharmaceutically acceptable salts are known in the art and are disclosed herein. As will be apparent to one skilled in the art, such salts can be converted to the corresponding free-base or to another salt using known methods.

Compounds of the invention can generally be prepared using the synthetic routes illustrated in the Schemes indicated below. Starting materials can be prepared by procedures described in these schemes or by procedures that would be well known to one of ordinary skill in organic chemistry. The variables used in the schemes are as defined below or as in the claims. The following five Schemes describe the preparation of compounds of the present invention. Scheme 1 shows the preparation of a benzazepine derivative.

5. After basic hydrolysis with, for example, potassium hydroxide in an aqueous ethanol media, the amine 6 is obtained.

Scheme 2 shows the preparation of chlorobenzazepine.

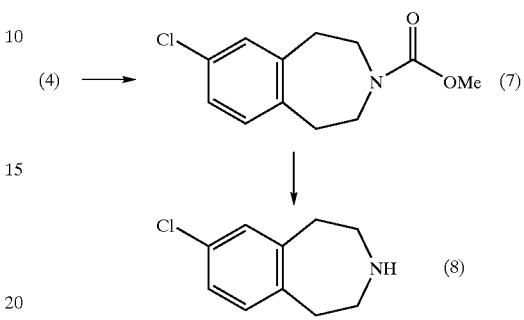

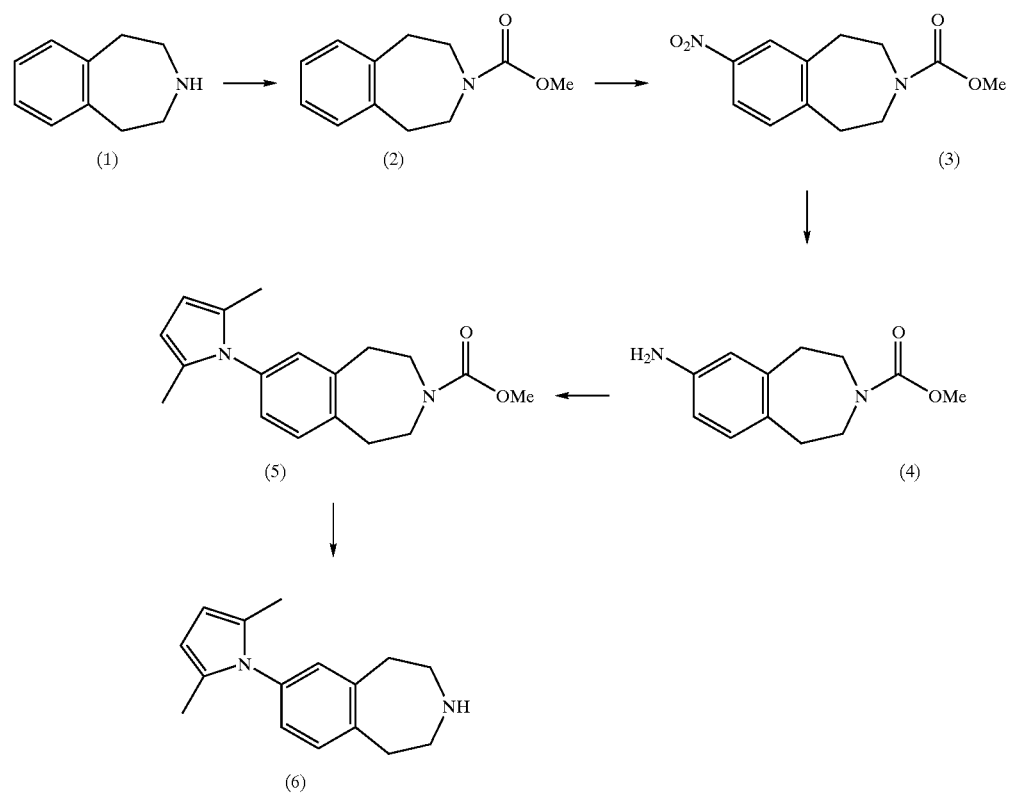

Compound 4 is converted to the corresponding chloro compound 7 by reacting with (butyl) nitrite and copper(II) chloride. Basic hydrolysis leads to removal of the protecting group to form the amine 8.

Benzazepine 1 is protected as the methylcarbamate 2 and then nitrated to give the nitro compound 3. Reduction with zinc dust in the presence of calcium chloride in 78% ethanol results in the formation of the amino compound 4, which is reacted with acetonylacetone to form the pyrrole compound Scheme 3 shows the preparation of methylchlorobenzazepine.

Scheme 3

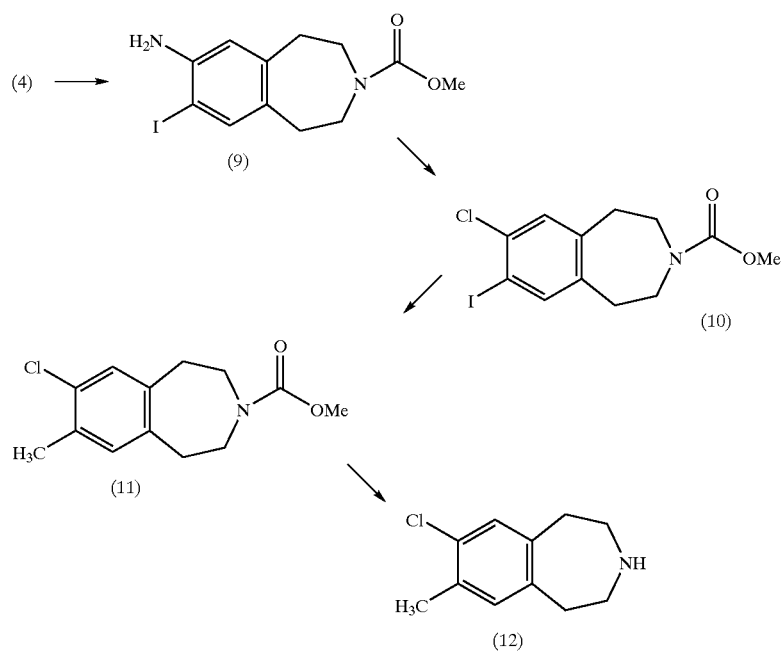

Compound 4 is iodinated with iodine monochloride to provide the iodo compound 9 followed by reaction with (butyl) nitrite and copper(II) chloride to give compound 10. Metal-halogen exchange with (t-butyl) lithium followed by quenching the generated anion with methyl iodide generates the methyl compound 11, which is hydrolyzed to form compound 12.

Schemes 4 and 5 show alternative methods for the preparation of a substituted benzazepine.

Scheme 4

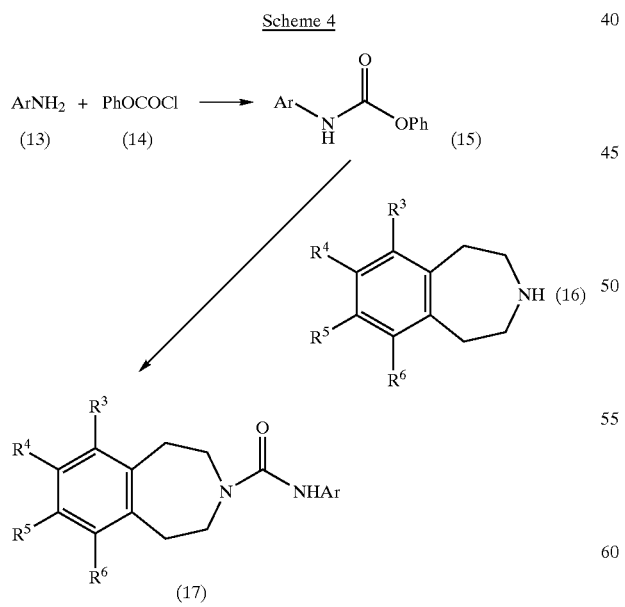

Compounds of Formula I can be prepared by the reactions outlined in Scheme 4. The substituted aryl amines 13 react with phenyl chloroformate (14) in the presence of triethyl amine in dichloromethane to form the carbamate 15. The generated carbamate 15 is then reacted with the amines 16 in N,N-dimethylformamide in the presence of triethyl amine to form the ureas 17.

Scheme 5

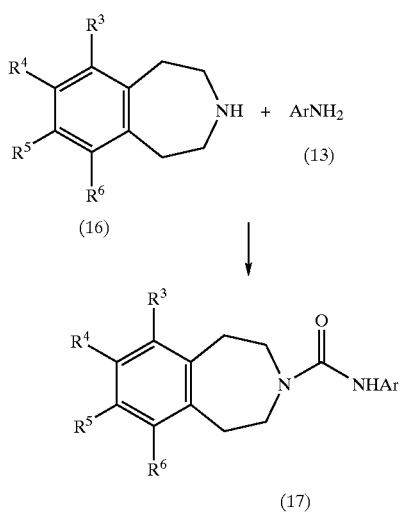

Compounds of Formula I can also be prepared by the reactions outlined in Scheme 5. The amines 16 react with triphosgene in the presence of diisopropyl ethylamine in dichloromethane to form the chloroformamide as the intermediate, which is reacted with the aryl amine 13 to lead to the formation of the ureas 17.

Preparation of the guanidine compound is depicted in Scheme 6. Compound 20 is converted to compound 21 by reaction with urea. The thiourea 22 can be obtained by treating compound 21 with $H_2S$ or Lawesson's reagent. Treatment of 22 with a methylating reagent such as methyl iodide or dimethyl sulphate provides compound 23, which when react with another amine R₁R₂NH, the guanidine compound 24 is formed (see Y. Yamamoto et. al. in "The Chemistry of Amidines and Imidates" Vol. 2, Chapt. 10, Patai, S.; Rappoport, Z. eds. John Wiley & Sons: New York, 1991).

Scheme 6

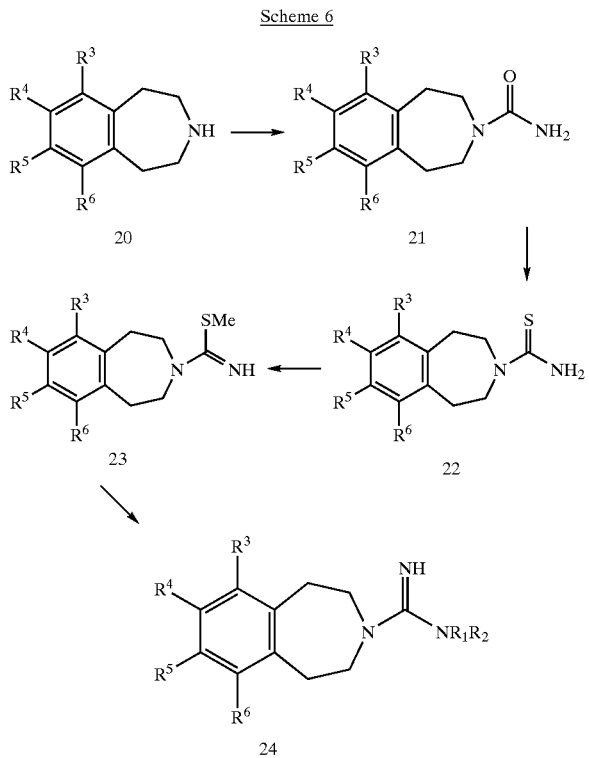

Preparation of the cyanoguanidine compound is depicted in Scheme 7. Amine 30 can be converted to the O-phenyl ether 31 by reacting with diphenylcyano-carbonimidate. This O-phenyl ether can react with the amine compound 20 in the presence of trimethylaluminum to form the desired cyanoguanidine 32 (see K. S. Atwal et. al., *Tetrahedron Lett.*, 1994, 35, 8085–8088).

Scheme 7

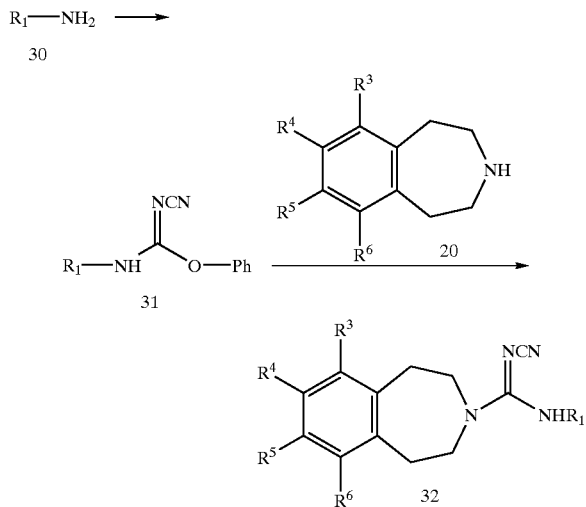

In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, carbonate salts, and the like salts. Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Compounds of the present invention can conveniently be administered in a pharmaceutical composition containing the compound in combination with a suitable excipient. Such pharmaceutical compositions can be prepared by methods and contain excipients which are well known in the art. A generally recognized compendium of such methods and ingredients is Remington's Pharmaceutical Sciences by E. W. Martin (Mark Publ. Co., 15th Ed., 1975). The compounds and compositions of the present invention can be administered parenterally, for example, by intravenous, intraperitoneal or intramuscular injection, topically, orally, or rectally.

For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The compounds or compositions can also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

Pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol, for example, glycerol, propylene glycol, liquid polyethylene glycols, and the like; vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions can be prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers. Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Useful dosages of the compounds of Formula I can be determined by comparing their in vitro activity, and in vivo activity in animal models. Methods for the extrapolation of effective dosages in mice, and other animals, to humans are known to the art; for example, see U.S. Pat. No. 4,938,949.

The compound is conveniently administered in unit dosage form; for example, containing about 0.05 mg to about 500 mg, conveniently about 0.1 mg to about 250 mg, most conveniently, about 1 mg to about 150 mg of active ingredient per unit dosage form. The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

The compositions can conveniently be administered orally, sublingually, transdermally, or parenterally at dose levels of about 0.01 to about 150 mg/kg, preferably about 0.1 to about 50 mg/kg, and more preferably about 0.1 to about 10 mg/kg of mammal body weight.

For parenternal administration the compounds are presented in aqueous solution in a concentration of from about 0.1 to about 10%, more preferably about 0.1 to about 7%. The solution may contain other ingredients, such as emulsifiers, antioxidants or buffers.

The exact regimen for administration of the compounds and compositions disclosed herein will necessarily be dependent upon the needs of the individual subject being treated, the type of treatment and, of course, the judgment of the attending practitioner.

The ability of a compound of the invention to act as a 5-HT receptor agonist or antagonist can also be determined using in vitro and in vivo assays that are known in the art. The invention provides compounds of formula I that act as either agonists or as antagonists of one or more 5-HT receptor subtypes. The compounds exemplified herein are 5-HT ligands, which typically displace a radio-labeled test ligand from one or more 5-HT receptor subtype at a concentration of, for example, about 1 micromolar ($\mu$M). The procedures used for testing such displacement are well known and would be readily available to one skilled in the art. See for example, L. W. Fitzgerald et al., *Mol. Pharmacol*, 2000, 57, 1, 75–81; and D. B. Wainscott, et al., *J. Pharmacol Exp Ther*, 1996, 276, 2, 720–727.

DESCRIPTION OF PREFERRED EMBODIMENTS

Preparation 1: Preparation of 7-(2,5-dimethyl-1H-pyrrol-1-yl)-2,3,4,5-tetrahydro-1H-3-benzazepine Step a. Methyl 1,2,4,5-tetrahydro-3H-3-benzazepine-3-carboxylate

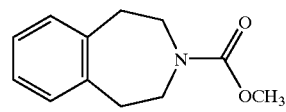

A flame-dried, 2-L, three-necked flask was charged with 2,3,4,5-tetrahydro-1H-3-benzazepine (95.0 g, 0.645 mol), sodium bicarbonate (108.4 g, 1.29 mol), THF (600 mL), and water (600 mL). The flask was cooled to 0° C. and methyl chloroformate (62.3 mL, 0.81 mol) was added dropwise over 30 min. The bath was removed and the mixture stirred at room temperature for 16 h. EtOAc was added, the mixture separated, and the aqueous layer was extracted with additional EtOAc. The combined organic layers was concentrated to give 133 g (100%) of the title product as a clear oil which crystallizes at room temperature: $^1$H NMR (300 MHz, CDCl$_3$) δ 7.15–7.13 (m, 4H), 3.76 (s, 3H), 3.71–3.53 (m, 4H), 2.99–2.82 (m, 4H); MS (EI) m/z 206 (MH$^+$).

Step b. Methyl 7-nitro-1,2,4,5-tetrahydro-3H-3-benzazepine-3-carboxylate and methyl 6-nitro-1,2,4,5-tetrahydro-3H-3-benzazepine-3-carboxylate (respectively)

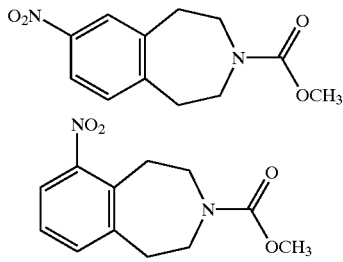

A 2-L, three-necked flask was charged with methyl 1,2,4,5-tetrahydro-3H-3-benzazepine-3-carboxylate (132.4 g, 0.645 mol) and sulfuric acid (400 mL). In a separate flask ammonium nitrate (54.2 g, 0.677 mol) was added to an ice-brine-bath cooled solution of sulfuric acid (400 mL) at −5° C., and stirred until homogeneous. The ammonium nitrate/sulfuric acid solution was added drop-wise over 1 h to the solution of 1,2,4,5-tetrahydro-3H-3-benzazepine-3-carboxylate in sulfuric acid at −5° C. After 1.5 h the solution was poured onto ice (2 L). The aqueous mixture was extracted first with EtOAc and then with $CH_2Cl_2$. The organic layers were concentrated and dried over magnesium sulfate to give 59.5 g of a orange oil (37%). The oil was subjected to preparative HPLC and the isomers separated to give pure samples of the title compounds methyl 6-nitro-1,2,4,5-tetrahydro-3H-3-benzazepine-3-carboxylate (1%) and methyl 7-nitro-1,2,4,5-tetrahydro-3H-3-benzazepine-3-carboxylate (20%). For methyl 7-nitro-1,2,4,5-tetrahydro-3H-3-benzazepine-3-carboxylate: IR (diffuse reflectance) 1693, 1517, 1471, 1440, 1415, 1345, 1318, 1310, 1270, 1243, 1199, 1108, 953, 895, 751 cm$^{-1}$; Anal. Calcd for $C_{12}H_{14}N_2O_4$: C, 57.59; H, 5.64; N, 11.19. Found: C, 57.56; H, 5.79; N, 11.19. For methyl 6-nitro-1,2,4,5-tetrahydro-3H-3-benzazepine-3-carboxylate: $^1$H NMR (300 MHz, CDCl$_3$) δ 7.54 (dd, J=1, 8 Hz, 1H), 7.35–7.33 (m, 1H), 7.24 (t, J=8 Hz, 1H), 3.71 (s, 3H), 3.70–3.61 (m, 4H), 3.08–2.96 (m, 4H); MS (FAB) m/z 251 (MH$^+$); HRMS (FAB) calcd for $Cl_{12}H_{14}N_2O_4$+H 251.1032, found 251.1040; Anal. Calcd for $Cl_{12}H_{14}N_2O_4$: C, 57.59; H, 5.64; N, 11.19. Found: C, 57.41; H, 5.69; N, 11.22.

Step c. Methyl 7-amino-1,2,4,5-tetrahydro-1H-3-benzazepine-3-carboxylate

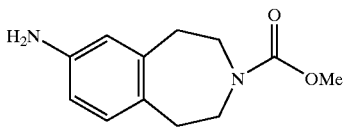

A mixture of methyl 7-nitro-1,2,4,5-tetrahydro-3H-3-benzazepine-3-carboxylate (12.51 g, 50.00 mmol), zinc (98.07 g, 1,500 mmol) and calcium chloride (2.77 g, 25.00 mmol) in 78% ethanol (500.0 mL) was refluxed for 3 h and filtered in hot. The filtrate was concentrated in vacuo to dryness and the residue was recrystalized from EtOAc/hexanes to give 8.65 g (79%) of colorless solid as the desired product: mp 95–97° C.; $^1$H NMR (300 MHz, CDCl$_3$) δ 6.89 (d, J=7.5 Hz, 1H), 6.47–6.44 (m, 2H), 3.73 (s, 3H), 3.55 (br, 6H), 2.78 (br, 4H); MS (EI) m/z 221 (MH$^+$).

Step d. Methyl 7-(2,5-dimethyl-1H-pyrrol-1-yl)-1,2,4,5-tetrahydro-3H-3-benzazepine-3-carboxylate

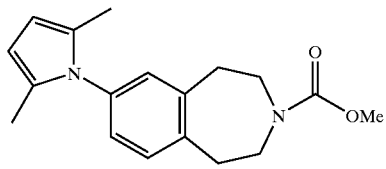

A mixture of 7-amino-2,3,4,5-tetrahydro-1H-3-benzazepine (2.20 g, 10.0 mmol), acetonylacetone (6.84 g, 60.0 mmol) and p-toluenesulfonic acid monohydrate (0.019 g, 0.10 mmol) in toluene (120 mL) was refluxed for 48 h with a Dean-Stark tube. Toluene was removed in vacuo and the residue was treated with chloroform (200 mL) and water (200 mL) and separated. The aqueous layer was extracted with chloroform (2×200 mL). The combined chloroform solution was dried over MgSO$_4$ and filtered. The filtrate was concentrated in vacuo to dryness and the residue was subjected to column chromatography (EtOAc:hexanes, 1:9) to give 1.56 g (52%) of colorless oil as the desired product: $^1$H NMR (300 MHz, CDCl$_3$) δ 7.19 (d, J=7.5 Hz, 1H), 6.99–6.96 (m, 2H), 5.88 (s, 2H), 3.75 (s, 3H), 3.65 (br, 4H), 2.93 (br, 4 H), 2.06 (s, 6H); MS (EI) m/z 299 (MH$^+$).

Step e. 7-(2,5-Dimethyl-1H-pyrrol-1-yl)-2,3,4,5-tetrahydro-1H-3-benzazepine

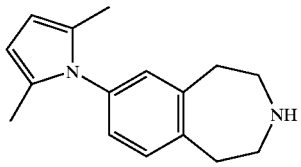

A mixture of methyl 7-(2,5-dimethyl-1H-pyrrol-1-yl)-1,2,4,5-tetrahydro-3H-3-benzazepine-3-carboxylate (0.73 g, 2.45 mmol) and potassium hydroxide (0.83 g, 14.7 mmol) in EtOH:H$_2$O (30.0 mL, 1:1) was refluxed for 16 h. After cooling down to room temperature, the mixture was concentrated in vacuo and water was added (40.0 mL). The aqueous solution was extracted with EtOAc (3×60.0 mL). The combined EtOAc solution was extracted with 1 N hydrochloric acid. The acidic solution was basified with ammonia and extracted with chloroform (3×60.0 mL). The combined chloroform solution was dried over MgSO$_4$ and filtered. The filtrate was concentrated in vacuo to dryness to give 0.36 g (61%) of colorless oil as the desired product: IR (film) 2972, 1611, 1581, 1520, 1503, 1456, 1434, 1340, 1320, 1145, 972, 752 cm$^{-1}$; $^1$H NMR (300 MHz, CDCl$_3$) δ 7.17 (d, J=8.4 Hz, 1H), 6.97–6.94 (m, 2H), 6.02 (s, 2H), 3.03–2.92 (m, 8H), 2.05 (s, 6H); MS (EI) m/z 240 (M$^+$); HRMS (FAB) cacld. for $C_{16}H_{20}N_2$+H: 241.1705, found: 241.1709.

Preparation 2: Preparation of 7-chloro-2,3,4,
5tetrahydro-1H-3-benzazepine

Step a. Methyl 7-chloro-1,2,4,5-tetrahydro-3H-3-benzazepine-3-carboxylate

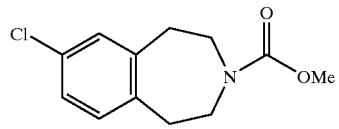

To a mixture of copper (II) chloride (2.00 g, 14.9 mmol) and butyl nitrite (2.18 mL, 1.92 g, 18.6 mmol) in acetonitrile (45.0 mL) was added the solution of methyl 7-amino-2,3,4,5-tetrahydro-1H-3-benzazepine-3-carboxylate (2.74 g, 12.4 mmol) in acetonitrile (26.0 mL) dropwise. The resulted mixture was stirred at room temperature for 16 h. Water (100.0 mL) was added. The aqueous solution was extracted with EtOAc (3×100.0 mL). The combined EtOAc solution was dried over $MgSO_4$ and filtered. The filtrate was concentrated in vacuo to dryness and the residue was subjected to column chromatography (EtOAc:hexanes, 1:6) to give 2.35 g (79%) of colorless oil as the desired product: $^1H$ NMR (300 MHz, $CDCl_3$) δ 7.14–7.04 (m, 3H), 3.75 (s, 3H), 3.59 (br, 4H), 2.89 (br, 4H); MS (EI) m/z 240 ($MH^+$).

Step b. 7-Chloro-2,3,4,5-tetrahydro-1H-3-benzazepine

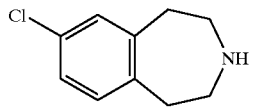

Following the procedure of Preparation 1(e), using methyl 7-chloro-1,2,4,5-tetrahydro-3H-3-benzazepine-3-carboxylate as the starting material, the title compound was prepared as a colorless oil (52%): IR (film) 2933, 1596, 1571, 1490, 1458, 1430, 1407, 1295, 1275, 962, 949, 816 $cm^{-1}$; $^1H$ NMR (300 MHz, $CDCl_3$) δ 7.08–7.00 (m, 3H), 2.96–2.92 (m, 4H), 2.89–2.87 (m, 4H); $^{13}C$ NMR (100 MHz, $CDCl_3$) δ 144.2, 140.8, 131.4, 130.5, 129.1, 125.9, 48.6, 48.5, 40.0, 39.7; MS (EI) m/z 182 ($MH^+$); HRMS (FAB) cacld. for $C_{10}H_{12}ClN+H$: 182.0737, found: 182.0730.

Preparation 3: Preparation of 7-Chloro-8-methyl-2,
3,4,5-tetrahydro-1H-3-benzazepine Step a. Methyl 7-amino-8-iodo-1,2,4,5-tetrahydro-1H-3-benzazepine-3-carboxylate

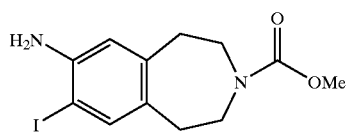

To a mixture of methyl 7-amino-1,2,4,5-tetrahydro-1H-3-benzazepine-3-carboxylate (2.20 g, 10.0 mmol) and calcium carbonate (2.00 g, 20.0 mmol) in MeOH (25.0 mL) was added the solution of iodo monochloride (1.79 g, 11.0 mmol) in MeOH (75.0 mL) at −30° C. The mixture was then stirred at room temperature for 16 h and filtered through a pad of celite. The filtrate was concentrated in vacuo to dryness. The residue was triturated and heated with EtOAc and filtered. The filtrate was washed with sodium sulfite solution (100 mL) and the aqueous layer was extracted with EtOAc (100 mL). The combined EtOAc solution was dried over $MgSO_4$ and filtered. The filtrate was concentrated in vacuo to dryness to give 3.28 g (77%) of light brown solid as the desired product: $^1H$ NMR (300 MHz, $CDCl_3$) δ 7.31 (s, 1H), 6.48 (s, 1H), 4.04 (br, 2H), 3.69 (s, 3H), 3.49 (br, 4H), 2.68 (br, 4H); MS (EI) m/z 347 ($MH^+$).

Step b. Methyl 7-chloro-8-iodo-1,2,4,5-tetrahydro-1H-3-benzazepine-3-carboxylate

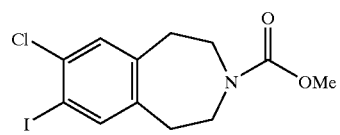

Following the procedure of Preparation 2(a), using methyl 7-amino-8-iodo-1,2,4,5-tetrahydro-3H-3-benzazepine-3-carboxylate as the starting material, the title compound was prepared as a colorless oil (97%): $^1H$ NMR (300 MHz, $CDCl_3$) δ 7.53 (s, 1H), 7.13 (s, 1H), 3.69 (s, 3H), 3.51 (br, 4H), 2.77 (br, 4H).

Step c. Methyl 7-chloro-8-methyl-1,2,4,5-tetrahydro-1H-3-benzazepine-3-carboxylate

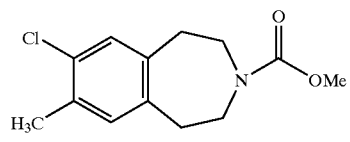

To a solution of methyl 7-chloro-8-iodo-1,2,4,5-tetrahydro-1H-3-benzazepine-3-carboxylate (0.90 g, 2.50 mmol) in THF (25.0 mL) was added t-BuLi (4.07 mL, 5.50 mmol) at −95° C. and followed by the addition of methyl iodide (0.62 mL, 0.28 g, 2.00 mmol). The resulted mixture was stirred at room temperature for 1 h and $NH_4Cl$ solution was added. After water (25.0 mL) and EtOAc (25.0 ml) were added, the layers were separated and the aqueous layer was extracted with EtOAc (2×25.0 mL). The combined EtOAc solution was dried over $MgSO_4$ and filtered. The filtrate was concentrated in vacuo to dryness. The residue was subjected to column chromatography (EtOAc:hexanes, 1:3) to give 0.55 g (73%) of colorless solid as the desired product: mp 96–97° C.; IR (KBr) 3025, 3014, 3003, 2940, 2914, 2860, 2842, 1697, 1567, 1531, 1489, 1468, 1465, 1379, 1295, 1272, 1242 $cm^{-1}$; $^1H$ NMR (300 MHz, $CDCl_3$) δ 7.10 (s, 1H), 6.97 (s, 1H), 3.74 (s, 3H), 3.56 (br, 4H), 2.83 (br, 4H), 2.30 (s, 3H); $^{13}C$ NMR (100 MHz, $CDCl_3$) δ 156.2, 139.9, 139.4, 133.7, 132.5, 131.8, 130.1, 52.8, 52.7, 46.9, 46.6, 37.2, 19.3; MS (EI) m/z 253 ($M^+$); Anal. Calcd. for $C_{13}H_{16}ClNO_2+0.25H_2O$: C, 60.47; H, 6.44; N, 5.42. Found: C, 60.78; H, 6.33; N, 5.43.

Step d. 7-Chloro-8-methyl-2,3,4,5-tetrahydro-1H-3-benzazepine

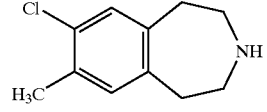

Following the procedure of Preparation 1(e), using methyl 7-chloro-8-methyl-1,2,4,5-tetrahydro-3H-3-benzazepine-3-carboxylate as the starting material, the title compound was prepared as a colorless oil (53%): $^1H$ NMR (300 MHz, $CDCl_3$) δ 7.07 (s, 1H), 6.95 (s, 1H), 2.92 (m, 4H), 2.86 (m, 4H); MS (EI) m/z 196 ($MH^+$), 198 ($MH^+$).

EXAMPLE 1

N-{6-[(2-methylpyridin-3-yl)oxy]pyridin-3-yl}-1,2,4,5-tetrahydro-3H-3-benzazepine-3-carboxamide

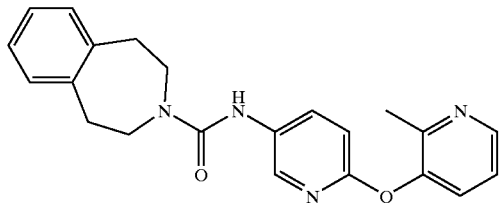

To a solution of phenyl chloroformate (1.51 mL, 1.54 g, 9.82 mmol) in dichloromethane (30.0 mL) was added the solution of 6-[(2-methylpyridin-3-yl)oxy]pyridin-3-amine (1.32 g, 6.54 mmol) and triethylamine (1.37 mL, 0.99 g, 9.82 mmol) in dichloromethane (35.0 mL) dropwise at −20° C. The resulted solution was stirred at −20° C. for 1 h and warmed to room temperature. The mixture was washed with sodium bicarbonate solution and dried with magnesium sulfate. After filtration, the filtrate was concentrated in vacuo to dryness. The residue was dissolved in N,N-dimethylformamide (41.0 mL). To this solution was added the solution of 2,3,4,5-tetrahydro-1H-3-benzazepine (0.96 g, 6.54 mmol) and triethylamine (1.00 mL, 0.73 g, 7.20 mmol) in N,N-dimethylformamide (24.0 mL). The resulted mixture was heated at 100° C. for 1 h. After cooling to room temperature, water (100 mL) and ethyl acetate (100 mL) were added and separated. The aqueous solution was extracted three times with ethyl acetate. The organic solution was dried over magnesium sulfate and filtered. The filtrate was concentrated in vacuo to dryness and the residue was subjected to column chromatography (EtOAc:hexanes, 3:1) to give 2.08 g (85%) of colorless solid as the desired product: mp 171–173° C.; IR (KBr) 3321, 2948, 2908, 1659, 1611, 1592, 1540, 1482, 1447, 1414, 1365, 1307, 1282, 1276, 1249, 1225, 1192, 1174, 1112, 950, 895, 830, 760 cm$^{-1}$; $^1$H NMR (300 MHz, CDCl$_3$) δ 8.34–8.31 (m, 1H), 8.00–7.94 (m, 2H), 7.32 (dd, J=8.1, 1.4 Hz, 1H), 7.16–7.10 (m, 5H), 7.03 (s, 1H), 6.88 (d, J=8.7 Hz, 1H), 3.69–3.66 (m, 4H), 3.00–2.96 (m, 4H), 2.41 (s, 3H); MS (EI) m/z 375 (MH$^+$), 228; HRMS (FAB) cacld. for C$_{22}$H$_{22}$N$_4$O$_2$+H: 375.1281, found: 375.1816; Anal. Calcd. for C$_{22}$H$_{22}$N$_4$O$_2$: C, 70.57; H, 5.92; N, 14.96. Found: C, 70.13; H, 6.09; N, 14.79.

EXAMPLE 2

7-(2,5-Dimethyl-1H-pyrrol-1-yl)-N-{6-[(2-methylpyridin-3-yl)oxy]pyridin-3-yl}-1,2,4,5-tetrahydro-3H-3-benzazepine-3-carboxamide

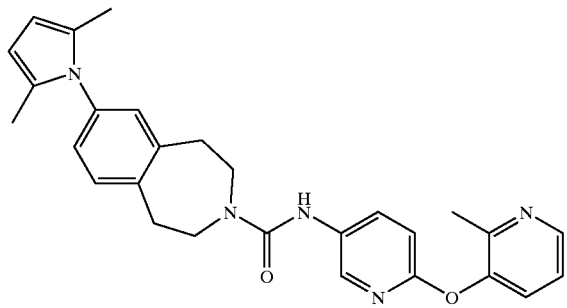

Following the procedure of Example 1, using 7-(2,5-dimethyl-1H-pyrrol-1-yl)-2,3,4,5-tetrahydro-1H-3-benzazepine and 6-[(2-methylpyridin-3-yl)oxy]pyridin-3-amine as the starting materials, the title compound was prepared as colorless solid (77%): mp 101° C. (dec.); IR (KBr) 3311, 2923, 1660, 1644, 1639, 1608, 1592, 1525, 1504, 1481, 1444, 1414, 1368, 1267, 1248, 1228, 1174, 1116, 947, 895, 827, 754, 722 cm$^{-1}$; $^1$H NMR (300 MHz, CDCl$_3$) δ 8.31–8.28 (m, 1H), 7.99–7.94 (m, 2H), 7.65, (s, 1H), 7.30 (dd, J=8.1, 1.4 Hz, 1H), 7.19–7.10 (m, 2H), 6.99–6.94 (m, 2H), 6.88–6.6.85 (m, 1H), 5.86 (s, 2H), 3.72–3.70 (br, 4H), 3.02–2.85 (m, 4H), 2.38 (s, 3H), 2.00 (s, 6H); $^{13}$C NMR (100 MHz, DMSO-d$_6$) δ 159.0, 154.9, 152.0, 149.1, 145.2, 141.1, 139.6, 139.1, 137.5, 133.7, 131.8, 130.7, 129.5, 128.8, 128.7, 126.3, 122.1, 111.1, 105.7, 47.0, 46.9, 37.4, 37.2, 19.5, 13.1; MS (EI) m/z 467 (M$^+$); HRMS (FAB) cacld. for C$_{28}$H$_{29}$N$_5$O$_2$+H: 468.2399, found: 468.2415; Anal. Calcd. for C$_{28}$H$_{29}$N$_5$O$_2$+0.5H$_2$O: C, 69.83; H, 6.27; N, 14.54. Found: C, 70.11; H, 6.41; N, 14.23.

EXAMPLE 3

7-Chloro-N-{6-[(2-methylpyridin-3-yl)oxy]pyridin-3-yl}-1,2,4,5-tetrahydro-3H-3-benzazepine-3-carboxamide

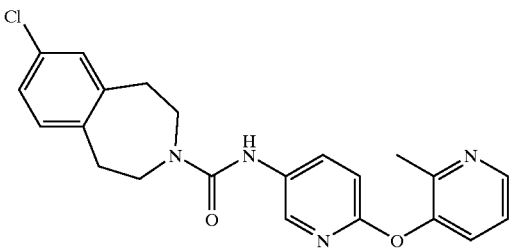

Following the procedure of Example 1, using 7-chloro-2,3,4,5-tetrahydro-1H-3-benzazepine and 6-[(2-methylpyridin-3-yl)oxy]pyridin-3-amine as the starting materials, the title compound was prepared as colorless oil (85%): IR (film) 3299, 3059, 1638, 1607, 1594, 1571, 1530, 1481, 1448, 1293, 1271, 1249, 1230, 1174, 1118, 856, 817 cm$^{-1}$; $^1$H NMR (300 MHz, CDCl$_3$) δ 8.32–8.31 (m, 1H), 7.99–7.95 (m, 2H), 7.62, (s, 1H), 7.32 (dd, J=8.2, 1.2 Hz, 1H), 7.17–7.01 (m, 4H), 6.89–6.86 (m, 1H), 3.66–3.65 (br, 4H), 2.95–2.87 (m, 4H), 2.39 (s, 3H); MS (EI) m/z 409 (MH$^+$); HRMS (FAB) cacld. for C$_{22}$H$_{21}$ClN$_4$O$_2$+H: 409.1431, found: 409.1438.

EXAMPLE 4

7-Chloro-8-methyl-N-{6-[(2-methylpyridin-3-yl)oxy]pyridin-3-yl}-1,2,4,5-tetrahydro-3H-3-benzazepine-3-carboxamide

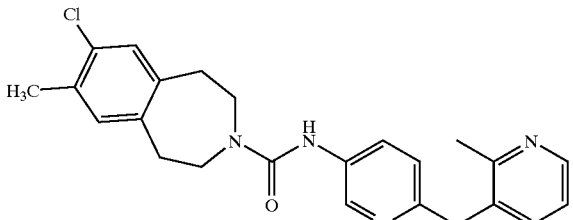

Following the procedure of Example 1, using 7-chloro-8-methyl-2,3,4,5-tetrahydro-1H-3-benzazepine and 6-[(2-methylpyridin-3-yl)oxy]pyridin-3-amine as the starting materials, the title compound was prepared as colorless oil (79%): IR (film) 3299, 3058, 1638, 1608, 1593, 1531, 1480, 1448, 1291, 1269, 1249, 1228, 1175, 1118, 843, 822, 800 cm$^{-1}$; $^1$H NMR (300 MHz, CDCl$_3$) δ 8.34–8.33 (m, 1H), 8.01–7.94 (m, 2H), 7.39–7.35 (dd, J=8.1, 1.2 Hz, 1H), 7.20–7.16 (m, 1H), 7.10 (s, 1H), 6.98 (s, 1H), 6.96 (s, 1H), 6.90 (d, J=8.8 Hz, 1H), 3.66–3.63 (m, 4H), 2.93–2.90 (m, 4H), 2.42 (s, 3H), 2.30 (s, 3H); MS (EI) m/z 423 (MH$^+$); HRMS (FAB) cacld. for C$_{23}$H$_{23}$ClN$_4$O$_2$+H: 423.1588, found: 423.1585.

EXAMPLE 5

1,2,4,5-Tetrahydro-benzo[d]azepine-3-carboxylic acid pyridin-3-ylamide

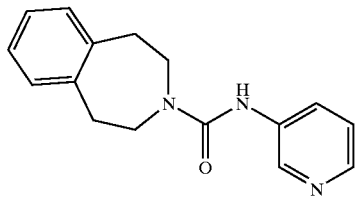

Following the procedure of Example 1, using 2,3,4,5-tetrahydro-1H-benzazepine and 3-aminopyridine as the starting materials, the title compound was prepared as colorless solid (75%): mp 144–146° C.; IR (KBr) 3346, 3262, 3050, 3026, 3010, 2941, 2910, 2896, 2872, 1638, 1592, 1535, 1522, 1485, 1471, 1285, 1270, 1234, 950, 796, 707, 748 cm$^{-1}$; $^1$H NMR (400 MHz, DMSO-d$_6$) δ 8.71 (s, 1H), 8.66 (d, J=2.4 Hz, 1H), 8.16 (dd, J=4.6, 1.3 Hz, 1H), 7.90–7.87 (m, 1H), 7.27 (dd, J=8.3, 4.6 Hz, 1H), 7.18–7.11 (m, 4H), 3.64–3.61 (m, 4H), 2.93–2.91 (m, 4H); $^{13}$C NMR (100 MHz, DMSO-d$_6$) δ 154.5, 142.6, 141.6, 140.7, 137.2, 129.5, 126.7, 126.1, 123.0, 46.3, 36.9; MS (EI) m/z 268 (MH$^+$); HRMS (FAB) cacld. for C$_{16}$H$_{17}$N$_3$O+H: 268.1450, found: 268.1459; Anal. Calcd. for C$_{16}$H$_{17}$N$_3$O: C, 71.89; H, 6.41; N, 15.72. Found: C, 71.83; H, 6.44; N, 15.63.

EXAMPLE 6

N-[2-Chloropyridin-3-yl]-1,2,4,5-tetrahydro-3H-3-benzazepine-3-carboxamide

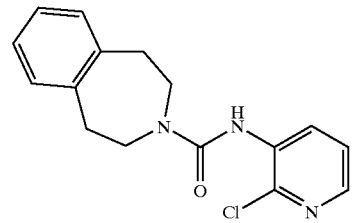

Following the procedure of Example 1, using 2,3,4,5-tetrahydro-1H-benzazepine and 2-chloro-3-aminopyridine as the starting materials, the title compound was prepared as a colorless solid (42%): mp 120–122° C.; IR (KBr) 3444, 3073, 3018, 2953, 2931, 2841, 1665, 1584, 1519, 1479, 1440, 1066, 1055, 760, 749, 708 cm$^{-1}$; $^1$H NMR (300 MHz, CDCl$_3$) δ 8.55–8.51 (dd, J=8.2, 1.7 Hz, 1H), 8.02–8.00 (dd, J=4.7, 1.7 Hz, 1H), 7.27–7.18 (m, 5H), 3.73–3.69 (m, 4H), 3.07–3.02 (m, 4H); $^{13}$C NMR (75 MHz, CDCl$_3$) δ 152.9, 141.6, 139.1, 138.7, 132.6, 129.3, 127.5, 127.1, 126.1, 122.6, 46.4, 36.6; MS (EI) m/z 301 (M$^+$); HRMS (FAB) calcd. for C$_{16}$H$_{16}$ClN$_3$O+H: 302.1060, found: 302.1052; Anal. Calcd. for C$_{16}$H$_{16}$N$_3$O: C, 63.68; H, 5.34; N, 13.92. Found: C, 63.54; H, 5.40; N, 13.82.

EXAMPLE 7

N-(6-chloropyridin-3-yl)-1,2,4,5-tetrahydro-3H-3-benzazepine-3-carboxamide

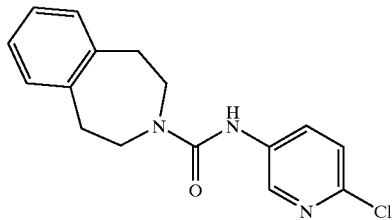

Following the procedure of Example 1, using 2,3,4,5-tetrahydro-1H-benzazepine and 5-amino-2-chloropyridine as the starting materials, the title compound was prepared as a colorless solid (74%): mp 170–172° C.; IR (KBr) 3339, 1662, 1638, 1586, 1525, 1513, 1469, 1418, 1371, 1305, 1285, 1271, 1244, 1233, 1226, 1214, 1193, 1112, 950, 831, 756 cm$^{-1}$; $^1$H NMR (400 MHz, CDCl$_3$) δ 8.26 (d, J=2.8 Hz, 1H), 8.00 (dd, J=8.7, 2.9 Hz, 1H), 7.25 (d, J=8.7 Hz, 1H), 7.18–7.13 (m, 4H), 6.77 (s, 1H), 3.70–3.68 (m, 4H), 3.03–3.00 (m, 4H); $^{13}$C NMR (100 MHz, CDCl$_3$) δ 154.3, 144.7, 140.5, 140.0, 135.4, 130.7, 130.0, 126.8, 124.1, 47.1, 37.5; MS (EI) m/z 301 (M$^+$); HRMS (FAB) calcd. for C$_{16}$H$_{16}$ClN$_3$O+H: 302.1060, found: 302.1070; Anal. Calcd. for C$_{16}$H$_{16}$N$_3$O; C, 63.68; H, 5.34; N, 13.92. Found: C, 63.27; H, 5.53; N, 13.92.

EXAMPLE 8

N-(6-Methoxypyridin-3-yl)-1,2,4,5-tetrahydro-3H-3-benzazepine-3-carboxamide

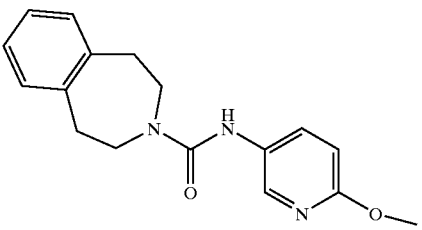

Following the procedure of Example 1, using 2,3,4,5-tetrahydro-1H-benzazepine and 5-amino-2-methoxypyridine as the starting materials, the title compound was prepared as a colorless solid (53%): 152–154° C.; IR (KBr) 3322, 3050, 3020, 2981, 2996, 2909, 2885, 2841, 1626, 1575, 1531, 1527, 1519, 1491, 1279, 1271, 1250, 1236, 1027, 821, 764, 759, 746 cm$^{-1}$; $^1$H NMR (400 MHz, CDCl$_3$) δ 8.00 (d, J=2.7 Hz, 1H), 7.77 (dd, J=8.9, 2.7 Hz, 1H), 7.17–7.12 (m, 4H), 6.71, (d, J=8.9 Hz, 1H), 6.43 (s, 1H), 3.90 (s, 3H), 3.72–3.66 (m, 4H), 3.02–3.00 (m, 4H); $^{13}$C NMR (100 MHz, CDCl$_3$) δ 160.8, 155.3, 140.3, 139.1, 133.8, 130.0, 129.7, 126.7, 110.5, 53.6, 47.1, 37.6; MS (EI) m/z 297 (M$^+$); HRMS (FAB) calcd. for C$_{17}$H$_{19}$N$_3$O$_2$+H: 298.1555, found: 298.1564; Anal. Calcd. for C$_{17}$H$_{19}$N$_3$O$_2$: C, 68.67; H, 6.44; N, 14.13. Found: C, 68.71; H, 6.51; N, 14.13.

EXAMPLE 9

N-[6-(4-Methoxyphenoxy)pyridin-3-yl]-1,2,4,5-tetrahydro-3H-3-benzazepine-3-carboxamide

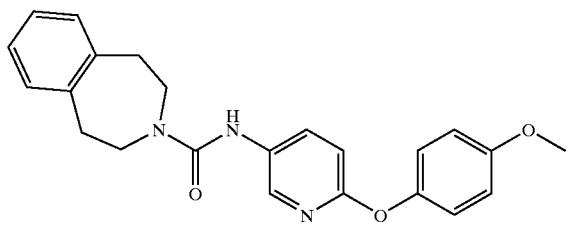

Following the procedure of Example 1, using 2,3,4,5-tetrahydro-1H-benzazepine and 6-(4-methoxyphenoxy)pyridin-3-amine as the starting materials, the title compound was prepared as a colorless solid (98%): mp 156–157° C.; IR (KBr) 3325, 3295, 2935, 2895, 1657, 1538, 1507, 1474, 1446, 1420, 1372, 1300, 1295, 1274, 1251, 1224, 1210, 1188, 1180, 1026, 950, 895, 851, 831, 760 cm$^{-1}$; $^1$H NMR (400 MHz, CDCl$_3$) δ 7.99 (d J=2.6 Hz, 1 H), 7.94 (dd, J=8.8, 2.7 Hz, 1 H), 7.18–7.12 (m, 4 H), 7.05–7.03 (m, 2H), 6.92–6.89 (m, 2H), 6.83 (d, J=8.8 Hz, 1H), 6.43 (s, 1H), 3.81 (s, 3H), 3.69–3.66 (m, 4H), 3.03–3.01 (m, 4H); $^{13}$C NMR (100 MHz, CDCl$_3$) δ 160.4, 156.4, 154.9, 147.9, 140.2, 139.4, 133.5, 131.1, 130.0, 126.7, 122.0, 114.8, 110.9, 55.6, 47.1, 37.6; MS (EI) m/z 390 (MH$^+$); HRMS (FAB) cacld for C$_{23}$H$_{23}$N$_3$O$_3$+H: 390.1817, found: 390.1821.

EXAMPLE 10

N-[6-(4-Chlorophenoxy)pyridin-3-yl]-1,2,4,5-tetrahydro-3H-3-benzazepine-3-carboxamide

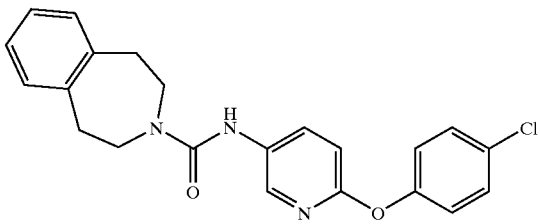

Following the procedure of Example 1, using 2,3,4,5-tetrahydro-1H-benzazepine and 6-(4-chlorophenoxy)pyridin-3-amine as the starting materials, the title compound was prepared as a colorless solid (33%): mp 135–137° C.; IR (KBr) 3370, 3074, 3063, 3037, 3025, 2927, 2897, 2865, 2839, 1632, 1610, 1588, 1568, 1536, 1519, 1476, 1451, 1288, 1275, 1247, 1201, 846, 834, 753 cm$^{-1}$; $^1$H NMR (400 MHz, CDCl$_3$) δ 8.01–7.97 (m, 2H), 7.34–7.30 (m, 2H), 7.18–7.11 (m, 4H), 7.05–7.01 (m, 2H), 6.89 (d, J=8.7 Hz, 1H), 6.54 (s, 1H), 3.69–3.66 (m, 4H), 3.03–3.00 (m, 4H); $^{13}$C NMR (100 MHz, CDCl$_3$) δ 159.2, 154.9, 153.2, 140.1, 139.3, 133.5, 131.9, 130.0, 129.7, 129.5, 126.8, 122.0, 111.7, 47.1, 37.5; MS (EI) m/z 393 (M$^+$); HRMS (FAB) calcd. for C$_{22}$H$_{20}$ClN$_3$O$_2$+H: 394.1322, found: 394.1320; Anal. calcd. for C$_{22}$H$_{20}$ClN$_3$O$_2$: C, 67.09; H, 5.12; N, 10.67. Found: C, 66.45; H, 5.16; N, 10.54.

EXAMPLE 11

N-[6-(2-Fluorophenoxy)pyridin-3-yl]-1,2,4,5-tetrahydro-3H-3-benzazepine-3-carboxamide

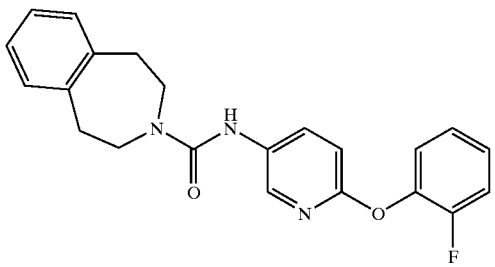

Following the procedure of Example 1, using 2,3,4,5-tetrahydro-1H-benzazepine and 6-(2-fluorophenoxy)pyridin-3-amine as the starting materials, the title compound was prepared as a colorless solid (83%): mp 170–172° C.; IR (KBr) 3361, 3083, 3061, 3041, 3029, 2987, 2933, 2906, 2885, 2861, 2849, 1637, 1635, 1607, 1592, 1550, 1531, 1526, 1516, 1499, 1482, 1454, 1295, 1283, 1266, 1250, 1233, 819, 756, 751 cm$^{-1}$; $^1$H NMR (400 MHz, CDCl$_3$) δ 7.99–7.94 (m, 2H), 7.22–7.12 (m, 8H), 6.93 (d, J=8.88 Hz, 1H), 6.51 (s, 1H), 3.68–3.65 (m, 4H), 3.02–2.99 (m, 4H); $^{13}$C NMR (100 MHz, CDCl$_3$) δ 159.1, 156.0, 154.9, 153.5, 141.5, 141.4, 140.2, 139.0, 133.6, 131.7, 130.0, 126.7, 125.9, 125.8, 124.6, 124.5, 123.7, 116.9, 116.8, 110.7, 47.1, 37.6; MS (EI) m/z 377 (M$^+$); HRMS (FAB) calcd. for C$_{22}$H$_{20}$FN$_3$O$_2$+H: 378.1617, found: 378.1616; Anal. calcd. for C$_{22}$H$_{20}$FN$_3$O$_2$+H$_2$O: C, 66.82; H, 5.61; N, 10.63. Found: C, 66.97; H, 5.22; N, 10.68.

EXAMPLE 12

N-[6-(2-isopropoxyphenoxy)pyridin-3-yl]-1,2,4,5-tetrahydro-3H-3-benzazepine-3-carboxamide

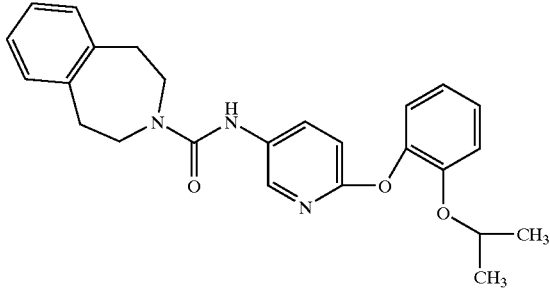

Following the procedure of Example 1, using 2,3,4,5-tetrahydro-1H-benzazepine and 6-(2-isopropoxyphenoxy)pyridin-3-amine as the starting materials, the title compound was prepared as a colorless solid (97%): mp 149–152° C.; IR (KBr) 3295, 3095, 3071, 3035, 2975, 2983, 2949, 1652, 1601, 1541, 1481, 1457, 1264, 1230, 1215, 1203, 1118, 821, 761, 754 cm$^{-1}$; $^1$H NMR (400 MHz, CDCl$_3$) δ 7.95–7.92 (m, 2H), 7.17–7.12 (m, 6H), 7.00–6.95 (m, 2H), 6.83 (d, J=8.6 Hz, 1H), 6.46 (s, 1H), 4.45 (qq, J=6.0 Hz, 1H), 3.68–3.66 (m, 4H), 3.03–3.00 (m, 4H), 1.16 (d, J=6.0 Hz, 6H); $^{13}$C NMR (100 MHz, CDCl$_3$) δ 160.2, 155.0, 150.1, 144.5, 140.2, 139.0, 133.1, 131.0, 130.0, 126.7, 125.6, 123.2, 121.4, 116.8, 110.4, 71.6, 47.1, 37.6, 22.1; MS (EI) m/z 417 (M$^+$); HRMS (FAB) calcd. for C$_{25}$H$_{27}$N$_3$O$_3$+H: 418.2130, found: 418.2133; Anal. Calcd. for C$_{25}$H$_{27}$N$_3$O$_3$: C, 71.92; H, 6.52; N, 10.06. Found: C, 72.07; H, 6.57; N, 10.03.

EXAMPLE 13

N-[6-(2-Methyl-4-chlorophenoxy)pyridin-3-yl]-1,2,4,5-tetrahydro-3H-3-benzazepine-3-carboxamide

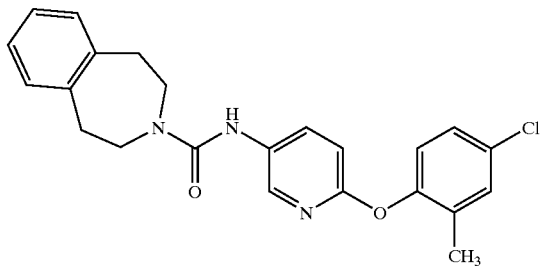

Following the procedure of Example 1, using 2,3,4,5-tetrahydro-1H-benzazepine and 6-(2-methyl-4-chlorophenoxy)pyridin-3-amine as the starting materials, the title compound was prepared as a colorless solid (75%): mp 151–153° C.; IR (KBr) 3349, 3076, 3066, 3030, 2944, 2926, 2895, 2865, 2829, 1630, 1608, 1588, 1535, 1518, 1474, 1248, 1176, 830, 824, 753 cm$^{-1}$; $^1$H NMR (400 MHz, CDCl$_3$) δ 7.97–7.95 (m, 2H), 7.23 (d, J=2.3 Hz, 1H), 7.18–7.12 (m, 5H), 6.93 (d, J=8.5 Hz, 1H), 6.86–6.84 (m, 1H), 6.49 (s, 1H), 3.68–3.66 (m, 4H), 3.02–3.00 (m, 4H), 2.15 (s, 3H); $^{13}$C NMR (100 MHz, CDCl$_3$) δ 159.5, 154.9, 151.1, 140.1, 139.4, 133.7, 132.5, 131.3, 131.1, 130.0, 129.9, 127.0, 126.7, 122.7, 110.7, 47.1, 37.5, 16.3; MS (EI) m/z 407 (M$^+$); HRMS (FAB) calcd. for C$_{23}$H$_{22}$ClN$_3$O$_2$+H: 408.1479, found: 408.1475; Anal. Calcd. for C$_{23}$H$_{22}$ClN$_3$O$_2$: C, 67.72; H, 5.44; N, 10.30. Found: C, 67.45; H, 5.47; N, 10.26.

EXAMPLE 14

N-[6-(3-Methyl-4-chlorophenoxy)pyridin-3-yl]-1,2,4,5-tetrahydro-3H-3-benzazepine-3-carboxamide

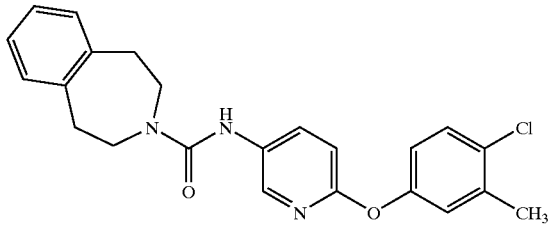

Following the procedure of Example 1, using 2,3,4,5-tetrahydro-1H-benzazepine and 6-(3-methyl-4-chlorophenoxy)pyridin-3-amine as the starting materials, the title compound was prepared as a colorless solid (92%): mp 171–173° C.; IR (KBr) 3368, 3072, 3062, 3034, 2952, 2928, 2877, 2863, 2839, 1631, 1609, 1586, 1549, 1534, 1518, 1488, 1472, 1450, 1439, 1292, 1282, 1265, 1248, 832, 823, 752 cm$^{-1}$; $^1$H NMR (400 MHz, CDCl$_3$) δ 8.01 (d, J=2.7 Hz, 1H), 7.97 (dd, J=8.8, 2.7 Hz, 1H), 7.30 (d, J=8.6 Hz, 1H), 7.18–7.12 (m, 4H), 6.97 (d, J=2.7 Hz, 1H), 6.89–6.85 (m, 2H), 6.58 (s, 1H), 3.69–3.67 (m, 4H), 3.03–3.00 (m, 4H), 2.34 (s, 3H); $^{13}$C NMR (100 MHz, CDCl$_3$) δ 159.4, 154.9, 153.1, 140.1, 139.3, 137.5, 133.6, 131.8, 130.0, 129.9, 129.8, 126.7, 123.0, 119.4, 111.7, 47.1, 37.5, 20.3; MS (EI) m/z 407 (M$^+$); HRMS (FAB) calcd. for C$_{23}$H$_{22}$ClN$_3$O$_2$+H: 408.1479, found: 408.1479; Anal. Calcd. for C$_{23}$H$_{22}$ClN$_3$O$_2$: C, 67.72; H, 5.44; N, 10.30. Found: C, 67.35; H, 5.44; N, 10.23.

EXAMPLE 15

N-[6-(2,4-Dichlorophenoxy)pyridin-3-yl]-1,2,4,5-tetrahydro-3H-3-benzazepine-3-carboxamide

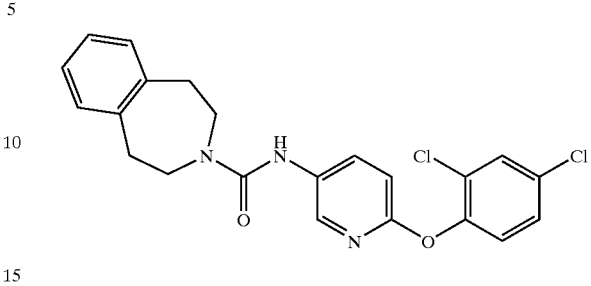

Following the procedure of Example 1, using 2,3,4,5-tetrahydro-1H-benzazepine and 6-(2,4-dichlorophenoxy)pyridin-3-amine as the starting materials, the title compound was prepared as a colorless solid (88%): mp 154–155° C.; IR (KBr) 3377, 3070, 3024, 3000, 2943, 2928, 2899, 1642, 1604, 1593, 1530, 1485, 1467, 1276, 1263, 1232, 1215, 863, 844, 819, 750, 734 cm$^{-1}$; $^1$H NMR (400 MHz, CDCl$_3$) δ 7.98 (dd, J=8.8, 2.7 Hz, 1H), 7.93 (d, J=2.7 Hz, 1H), 7.45 (d, J=2.4 Hz, 1H), 7.26–7.23 (m, 1H), 7.18–7.12 (m, 4H), 7.10 (d, J=8.6 Hz, 1H), 6.95 (d, J=8.8 Hz, 1H), 6.50 (s, 1H), 3.68–3.66 (m, 4H), 3.02–3.00 (m, 4H); $^{13}$C NMR (100 MHz, CDCl$_3$) δ 158.8, 154.9, 149.0, 140.1, 139.0, 133.7, 131.9, 130.5, 130.3, 130.0, 128.0, 126.8, 124.3, 111.1, 47.1, 37.5; MS (EI) m/z 428 (M$^+$–H), 426 (M$^+$–H); HRMS (FAB) calcd. for C$_{22}$H$_{19}$Cl$_2$N$_3$O$_2$+H: 428.0932, found: 428.0916; Anal. Calcd. for C$_{22}$H$_{19}$Cl$_2$N$_3$O$_2$: C, 61.69; H, 4.47; N, 9.81. Found: C, 61.73; H, 4.54; N, 9.75.

EXAMPLE 16

N-[6-(4-Chloro-3,5-dimethylphenoxy)pyridin-3-yl]-1,2,4,5-tetrahydro-3H-3-benzazepine-3-carboxamide

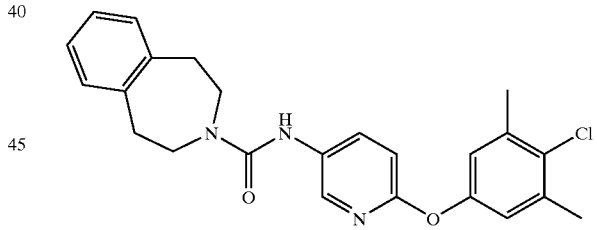

Following the procedure of Example 1, using 2,3,4,5-tetrahydro-1H-benzazepine and 6-(4-chloro-3,5-dimethylphenoxy)pyridin-3-amine as the starting materials, the title compound was prepared as a colorless solid (44%): mp 208–209° C.; IR (KBr) 3375, 2992, 2939, 2928, 2896, 2962, 2837, 1632, 1609, 1591, 1550, 1532, 1517, 1488, 1467, 1451, 1254, 1247, 1029, 843, 829, 754 cm$^{-1}$; $^1$H NMR (400 MHz, CDCl$_3$) δ 8.00 (d, J=2.7 Hz, 1H), 7.96, (dd, J=8.8, 2.7 Hz, 1H), 7.18–7.12 (m, 4H), 6.87 (d, J=8.8 Hz, 1H) 6.83 (s, 2H), 6.52 (s, 1H), 3.69–3.66 (m,4H), 3.02–3.00 (m, 4H), 2.35 (s, 6H); $^{13}$C NMR (100 MHz, CDCl$_3$) δ 159.6, 159.3, 154.9, 152.4, 140.2, 139.5, 137.6, 133.5, 131.6, 130.2, 130.0, 126.8, 120.6, 111.7, 47.1, 37.6, 20.9; MS (EI) m/z 421 (M$^+$); HRMS (FAB) calcd. for C$_{24}$H$_{24}$ClN$_3$O$_2$+H: 422.1635, found: 422.1635; Anal. calcd. for C$_{24}$H$_{24}$ClN$_3$O$_2$: C, 68.32; H, 5.73; N, 9.96. Found: C, 68.18; H, 5.81; N, 9.93.

EXAMPLE 17

N-Piperidin-3-yl-1,2,4,5-tetrahydro-3H-3-benzazepine-3-carboxamide

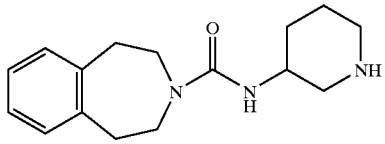

To a solution of 2,3,4,5-tetrahydro-1H-3-benzazepine (0.122 g, 0.825 mmol) and Hunig's base (0.17 mL, 0.128 g, 0.99 mmol) was added triphosgene (0.135 g, 0.454 mmol) at 0° C. The mixture was stirred at 0° C. for 1 hour and then at room temperature for 2 h. The mixture was again cooled to 0° C. and another portion of Hunig's base (0.78 mL, 0.576 g, 4.46 mmol) and 3-aminopiperidine dihydrochloride (0.0.25 g, 1.44 mmol) were added and the mixture was stirred at room temperature for 16 h. Sodium bicarbonate solution was added and the mixture was extracted twice with $CH_2Cl_2$. The combined organic layers was dried over $MgSO_4$ and filtered. The filtrate was concentrated in vacuo to dryness and the residue was subjected to column chromatography ($CH_2Cl_2$:MeOH:$NH_4Cl$, 90:10:1) to give 0.165 g (66%) of colorless solid as the desired product: mp 214–216° C.; IR (diffuse reflectance) 3105, 3059, 3030, 3017, 2999, 2988, 2978, 2941, 2910, 2901, 2841, 1635, 1592, 1511, 1470, 1451, 1420, 1387, 1378, 1303, 1254, 1223, 947, 905, 740 cm$^{-1}$; $^1$H NMR (400 MHz, DMSO-$d_6$) δ 7.15–7.10 (m, 4H), 3.63 (m, 1H), 3.34–3.31 (m, 5H), 3.20–3.10 (m, 1H), 2.92–2.77 (m, 6H), 2.05–1.97 (m, 1H), 1.76–1.72 (m, 1H), 1.56–1.46 (m, 2H); $^{13}$C NMR (100 MHz, DMSO-$d_6$) δ 163.4, 140.8, 129.1, 126.1, 48.9, 48.4, 47.3, 46.2, 36.4, 28.0, 22.4; MS (EI) m/z 273 (MH$^+$); HRMS (FAB) calcd for $C_{16}H_{23}N_3O$+H 274.1919, found 274.1923; Anal. calcd. for $Cl_{16}H_{23}N_3O$+HCl: C, 62.02; H, 7.81; N, 13.56. Found: C, 61.80; H, 7.75; N, 13.44.

EXAMPLE 18

N-(1-Azabicyclo[2.2.2]oct-3-yl)-1,2,4,5-tetrahydro-3H-3-benzazepine-3-carboxamide

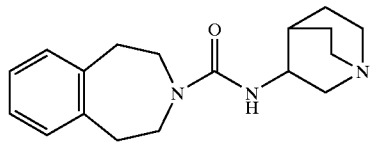

Following the procedure of Example 17, using 2,3,4,5-tetrahydro-1H-benzazepine and quinuclidin-3-amine as the starting materials, the title compound was prepared as a colorless solid (39%): mp>120° C. (dec.); IR (KBr) 3310, 3014, 2983, 2936, 2903, 2759, 2661, 2589, 2573, 2481, 1644, 1636, 1626, 1615, 1533, 1485, 1458, 1430, 1415, 1336, 1310, 1275, 1249, 1216, 948, 756 cm$^{-1}$; $^1$H NMR (400 MHz, DMSO-$d_6$) δ 7.15–7.09 (m, 4H), 6.68, (d, J=5.2 Hz, 1H), 4.02 (br, 1H), 3.56–3.46 (m, 5H), 3.14 (br, 5H), 2.84–2.83 (m, 4H), 2.07 (br, 2H), 1.84 (br, 2H), 1.65 (br, 1H); $^{13}$C NMR (100 MHz, DMSO-$d_6$) δ 156.6, 140.8, 129.5, 126.0, 51.2, 46.0, 45.4, 45.3, 44.8, 36.9, 24.5, 21.4, 17.0; MS (EI) m/z 300 (MH$^+$); HRMS (FAB) calcd. for $C_{18}H_{25}N_3O_2$+H: 300.2076, found: 300.2077; Anal. calcd. for $C_{18}H_{25}N_3O$+HCl+$H_2O$: C, 61.09; H, 7.69; N, 11.87. Found: C, 60.57; H, 7.89; N, 11.91.

EXAMPLE 19

N-[(3R)-1-Azabicyclo[2.2.2]oct-3-yl]-1,2,4,5-tetrahydro-3H-3-benzazepine-3-carboxamide

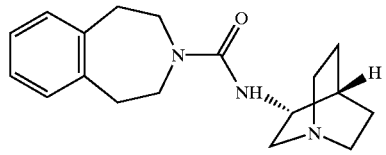

Following the procedure of Example 17, using 2,3,4,5-tetrahydro-1H-benzazepine and (S)-(−)-3-aminoquinuclidine dihydrochloride as the starting materials, the title compound was prepared as a colorless solid (64%): IR (diffuse reflectance) 3424, 2939, 2917, 2869, 2350, 2318, 1949, 1916, 1620, 1537, 1490, 1473, 1251, 945, 756, cm$^{-1}$. MS (FAB) m/z 300 (MH$^+$); HRMS (FAB) calcd for $C_{18}H_{25}N_3O$+H 300.2076, found 300.2077.

EXAMPLE 20

N-[(3S)-1-Azabicyclo[2.2.2]oct-3-yl]-1,2,4,5-tetrahydro-3H-3-benzazepine-3-carboxamide

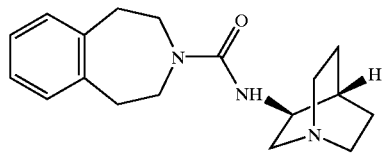

Following the procedure of Example 17, using 2,3,4,5-tetrahydro-1H-benzazepine and (R)-(−)-3-aminoquinuclidine dihydrochloride as the starting materials, the title compound was prepared as a colorless solid (44%): mp 128–132° C.; IR (diffuse reflectance) 2940, 2920, 2869, 2255, 1949, 1915, 1620, 1540, 1492, 1473, 1315, 1251, 1055, 945, 756, cm$^{-1}$; $^1$H NMR (CDCl$_3$) δ 7.16–7.10 (m, 4H), 4.61 (d, J=6 Hz, 1H), 3.95–3.87 (m, 1H), 3.59–3.56 (m, 4H), 3.40–3.34 (m, 1H), 2.97–2.94 (m, 4H), 2.89–2.75 (m, 4H), 2.51–2.46 (m, 1H), 1.95–1.92 (m, 1H), 1.69–1.64 (m, 3H), 1.56–1.45 (m, 1H); $^{13}$C NMR (100 MHz, CDCl$_3$) δ 157.1, 130.5, 129.9, 126.6, 56.8, 47.9, 47.5, 46.8, 46.7, 37.6, 26.2, 25.9, 20.3; MS (EI) m/z 299 (M$^+$); HRMS (FAB) calcd for $C_{18}H_{25}N_3O$+H 300.2076, found 300.2087.

The invention has been described with reference to various specific and preferred embodiments and techniques. However, it should be understood that many variations and modifications may be made while remaining within the spirit and scope of the invention.

What is claimed is:

1. A compound of Formula I:

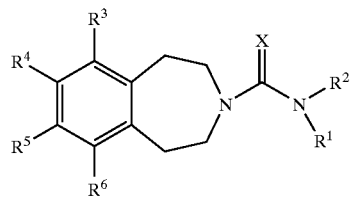

Formula I wherein
X is O, S, or N—$R_b$;
$R^1$ is —Y-Q-Z;
Y is heterocycle, substituted heterocycle, heteroaryl, or substituted heteroaryl,
Q is absent, —O—, —S(O)$_m$—, —NR$_a$—, or alkylene;
Z is aryl, substituted aryl, heterocycle, substituted heterocycle, heteroaryl, substituted heteroaryl, or absent provided that Q is also absent;
$R^2$ is H, $C_{1-8}$alkyl, or aryl($C_{1-8}$alkylene-);
$R^3$, $R^4$, $R^5$, and $R^6$ are each independently H, hydroxy, nitro, halo, cyano, $N_3$, amidine, guanidine, thioguanidine, cyanoguanidine, $C_{1-8}$alkyl, $C_{1-8}$haloalkyl, $C_{1-8}$alkoxy, $C_{1-8}$haloalkoxy, $C_{3-8}$cycloalkyl, aryl, heteroaryl, substituted heteroaryl, —S(O)NR$_c$R$_d$, —S(O)$_2$NR$_c$R$_d$, —NR$_c$R$_d$, —S(O)$_m$R$_a$, —C(=O)NR$_c$R$_d$, —C(=S)NR$_c$R$_d$, —N(R$_a$)—S(O)R$_a$, or —N(R$_a$)—S(O)$_2$R$_a$;
each $R_a$ is independently H, $C_{1-8}$alkyl, $C_{1-8}$alkanoyl, $C_{1-8}$alkoxycarbonyl, aryl, aryl($C_{1-8}$alkylene-), heteroaryl, heteroaryl($C_{1-8}$alkylene-), heterocycle, or heterocycle($C_{1-8}$alkylene-);
$R_b$ is hydrogen, $C_{1-8}$alkyl, $C_{1-8}$alkanoyl, $C_{1-8}$alkoxycarbonyl, aryl, aryl($C_{1-8}$alkylene-), heteroaryl, heteroaryl($C_{1-8}$alkylene-), heterocycle, or heterocycle($C_{1-8}$alkylene-);
each of $R_c$ and $R_d$ is independently H, $C_{1-8}$alkyl, $C_{1-8}$alkanoyl, $C_{1-8}$alkoxycarbonyl, aryl, aryl($C_{1-8}$alkylene-), heteroaryl, heteroaryl($C_{1-8}$alkylene-), heterocycle, or heterocycle($C_{1-8}$alkylene-); or $R_c$ and $R_d$ together with the nitrogen to which they are attached form azepino, piperazino, pyrrolidino, piperidino, morpholino, or thiomorpholino ring;
each m is independently 0, 1, or 2;
wherein heterocycle, heteroaryl, and substituted are as defined in the specification;
or a pharmaceutically acceptable salt thereof.

2. The compound of claim 1, wherein Y is heteroaryl or substituted heteroaryl.
3. The compound of claim 1, wherein Y is pyridin-3-yl or 2-halo-pyridin-3-yl.
4. The compound of claim 1, wherein Y is heterocycle or substituted heterocycle.
5. The compound of claim 1, wherein Y is piperidin-3-yl or quinuclidin-3-yl.
6. The compound of claim 1, wherein Y is pyridin-3-yl.
7. A compound of claim 1, wherein Y is heterocycle or heteroaryl, each substituted with hydroxy and Q and Z are both absent.
8. A compound of claim 1, wherein Q is —O—, and Z is substituted heteroaryl.
9. A compound of claim 1, wherein Q is —O—, and Z is substituted aryl.
10. A compound of claim 1, wherein Q is —O—, and Z is 2-methyl-pyridin-3-yl.
11. A compound of claim 1, wherein Q is —O—, and Z is alkoxy substituted phenyl.
12. A compound of claim 1, wherein Q is —O—, and Z is 4-halo substituted phenyl.
13. A compound of claim 1, wherein Q is —O—, and Z is halo and alkyl substituted phenyl.
14. A compound of claim 1, wherein Q is —O—, and Z is halo and dialkyl substituted phenyl.
15. A compound of claim 1, wherein Q is —O—, and Z is dihalo substituted phenyl.

16. The compound of claim 1, wherein the compound is a compound of Formula II:

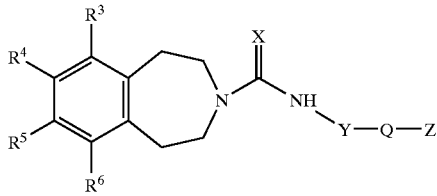

Formula II wherein $R^3$, $R^4$, $R^5$, $R^6$, Q, X, Y and Z are the same as in claim 1.

17. The compound of claim 16, wherein Y is heterocycle or substituted heterocycle.
18. The compound of claim 16, wherein Y is heteroaryl or substituted heteroaryl.
19. The compound of claim 1, wherein the compound is a compound of Formula III:

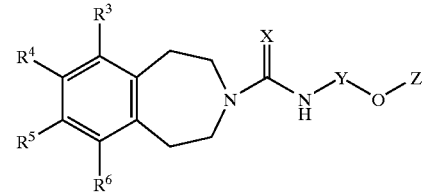

Formula III wherein $R^3$, $R^4$, $R^5$, $R^6$, X, Y and Z are the same as in claim 1.

20. The compound of claim 19, wherein Y is heterocycle or substituted heterocycle, and Z is aryl, substituted aryl, heterocycle, substituted heterocycle, heteroaryl, or substituted heteroaryl.
21. The compound of claim 19, wherein Y is heteroaryl or substituted heteroaryl, and Z is aryl, substituted aryl, heterocycle, substituted heterocycle, heteroaryl, or substituted heteroaryl.
22. The compound of claim 1, wherein $R^1$ is 6-(2-methyl-pyridin-3-yloxy)-pyridin-3-yl and X is O.
23. The compound of claim 1, wherein $R^2$ is H.
24. The compound of claim 1, wherein $R^2$ is $C_{1-8}$alkyl.
25. The compound of claim 1, wherein $R^2$ is aryl($C_{1-8}$alkylene-).
26. The compound of claim 1, wherein $R^3$ is —H.
27. The compound of claim 1, wherein $R^3$ is halo.
28. The compound of claim 1, wherein $R^3$ is alkyl.
29. The compound of claim 1, wherein $R^4$ is —H.
30. The compound of claim 1, wherein $R^4$ is substituted heteroaryl.
31. The compound of claim 1, wherein $R^4$ is 2,5-dimethylpyrrol-1-yl.
32. The compound of claim 1, wherein $R^4$ is halo.
33. The compound of claim 1, wherein $R^4$ is alkyl.
34. The compound of claim 1, wherein $R^5$ is —H.
35. The compound of claim 1, wherein $R^6$ is —H.
36. The compound of claim 1, wherein $R^6$ is halo.
37. The compound of claim 1, wherein $R^6$ is alkyl.
38. The compound of claim 16, wherein the compound is selected from the group consisting of N-{6-[(2-methylpyridin-3-yl)oxy]pyridin-3-yl}-1,2,4,5-tetrahydro-3H-3-benzazepine-3-carboxamide; 7-(2,5-dimethyl-1H-pyrrol-1-yl)-N-{6-[(2-methylpyridin-3-yl)oxy]pyridin-3-yl}-1,2,4,5-tetrahydro-3H-3-benzazepine-3-carboxamide;

7-chloro-N-{6-[(2-methylpyridin-3-yl)oxy]pyridin-3-yl}-1,2,4,5-tetrahydro-3H-3-benzazepine-3-carboxamide; 7-chloro-8-methyl-N-{6-[(2-methylpyridin-3-yl)oxy]pyridin-3-yl}-1,2,4,5-tetrahydro-3H-3-benzazepine-3-carboxamide; N-(6-methoxypyridin-3-yl)-1,2,4,5-tetrahydro-3H-3-benzazepine-3-carboxamide; N-[6-(4-methoxyphenoxy)pyridin-3-yl]-1,2,4,5-tetrahydro-3H-3-benzazepine-3-carboxamide; N-[6-(4-chlorophenoxy)pyridin-3-yl]-1,2,4,5-tetrahydro-3H-3-benzazepine-3-carboxamide; N-[6-(2-fluorophenoxy)pyridin-3-yl]-1,2,4,5-tetrahydro-3H-3-benzazepine-3-carboxamide; N-[6-(2-isopropoxyphenoxy)pyridin-3-yl]-1,2,4,5-tetrahydro-3H-3-benzazepine-3-carboxamide; N-[6-(2-methyl-4-chlorophenoxy)pyridin-3-yl]-1,2,4,5-tetrahydro-3H-3-benzazepine-3-carboxamide; N-[6-(3-methyl-4-chlorophenoxy)pyridin-3-yl]-1,2,4,5-tetrahydro-3H-3-benzazepine-3-carboxamide; N-[6-(2,4-dichlorophenoxy)pyridin-3-yl]-1,2,4,5-tetrahydro-3H-3-benzazepine-3-carboxamide; N-[6-(4-chloro-3,5-dimethylphonoxy)pyridin-3-yl]-1,2,4,5-tetrahydro-3H-3-benzazepine-3-carboxamide; or a pharmaceutically acceptable salt thereof.

39. The compound of claim 19, wherein the compound is selected from the group consisting of N-{6-[(2-methylpyridin-3-yl)oxy]pyridin-3-yl}-1,2,4,5-tetrahydro-3H-3-benzazepine-3-carboxamide; 7-(2,5-dimethyl-1H-pyrrol-1-yl)-N-{6-[(2-methylpyridin-3-yl)oxy]pyridin-3-yl}-1,2,4,5-tetrahydro-3H-3-benzazepine-3-carboxamide; 7-chloro-N-{6-[(2-methylpyridin-3-yl)oxy]pyridin-3-yl}-1,2,4,5-tetrahydro-3H-3-benzazepine-3-carboxamide; 7-chloro-8-methyl-N-{6-[(2-methylpyridin-3-yl)oxy]pyridin-3-yl}-1,2,4,5-tetrahydro-3H-3-benzazepine-3-carboxamide; N-(6-methoxypyridin-3-yl)-1,2,4,5-tetrahydro-3H-3-benzazepine-3-carboxamide; N-[6-(4-methoxyphenoxy)pyridin-3-yl]-1,2,4,5-tetrahydro-3H-3-benzazepine-3-carboxamide; N-[6-(4-chlorophenoxy)pyridin-3-yl]-1,2,4,5-tetrahydro-3H-3-benzazepine-3-carboxamide; N-[6-(2-fluorophenoxy)pyridin-3-yl]-1,2,4,5-tetrahydro-3H-3-benzazepine-3-carboxamide; N-[6-(2-isopropoxyphenoxy)pyridin-3-yl]-1,2,4,5-tetrahydro-3H-3-benzazepine-3-carboxamide; N-[6-(2-methyl-4-chlorophenoxy)pyridin-3-yl]-1,2,4,5-tetrahydro-3H-3-benzazepine-3-carboxamide; N-[6-(3-methyl-4-chlorophenoxy)pyridin-3-yl]-1,2,4,5-tetrahydro-3H-3-benzazepine-3-carboxamide; N-[6-(2,4-dichlorophenoxy)pyridin-3-yl]-1,2,4,5-tetrahydro-3H-3-benzazepine-3-carboxamide; N-[6-(4-chloro-3,5-dimethylphonoxy)pyridin-3-yl]-1,2,4,5-tetrahydro-3H-3-benzazepine-3-carboxamide; or a pharmaceutically acceptable salt thereof.

40. A pharmaceutical composition comprising a compound of claim 1 and a pharmaceutically acceptable excipient.

41. A pharmaceutical composition comprising a compound of claim 16 and a pharmaceutically acceptable excipient.

42. A pharmaceutical composition comprising a compound of claim 19 and a pharmaceutically acceptable excipient.

43. A pharmaceutical composition comprising a compound of claim 38 and a pharmaceutically acceptable excipient.

44. A pharmaceutical composition comprising a compound of claim 39 and a pharmaceutically acceptable excipient.

45. A radiolabeled compound which comprises a compound of claim 1 and one or more radioisotopes.

46. A radiolabeled compound which comprises a compound of claim 16 and one or more radioisotopes.

47. A radiolabeled compound which comprises a compound of claim 19 and one or more radioisotopes.

48. A radiolabeled compound which comprises a compound of claim 38 and one or more radioisotopes.

49. A radiolabeled compound which comprises a compound of claim 39 and one or more radioisotopes.

50. The radiolabeled compound of claim 45 wherein the one or more radioisotopes is selected from one or more carbon-11, fluorine-18, fluorine-19, iodine-123 or iodine-125.

51. The radiolabeled compound of claim 46 wherein the one or more radioisotopes is one or more carbon-11, fluorine-18, fluorine-19, iodine-123 or iodine-125.

52. The radiolabeled compound of claim 47 wherein the one or more radioisotopes is one or more carbon-11, fluorine-18, fluorine-19, iodine-123 or iodine-125.

53. The radiolabeled compound of claim 48 wherein the one or more radioisotopes is one or more carbon-11, fluorine-18, fluorine-19, iodine-123 or iodine-125.

54. The radiolabeled compound of claim 49 which comprises one or more carbon-11, fluorine-18, fluorine-19, iodine-123 or iodine-125.

55. A method for treating a disease or condition of the central nervous system in a mammal wherein the 5-HT$_{2C}$ receptor is implicated and modulation of 5-HT$_{2C}$ function is desired, comprising administering a therapeutically effective amount of a compound of claim 1 to the mammal, wherein the disease or condition is selected from the group consisting of anxiety, obesity, depression, panic disorder, a phobia and obsessive compulsive disorder.

56. A method for treating a disease or condition of the central nervous system in a mammal wherein the 5-HT$_{2c}$ receptor is implicated and modulation of 5-HT$_{2C}$ function is desired, comprising administering a therapeutically effective amount of a compound of claim 16 to the mammal, wherein the disease or condition is selected from the group consisting of anxiety, obesity, depression, panic disorder, a phobia and obsessive compulsive disorder.

57. A method for treating disease or condition of the central nervous system in a mammal wherein the 5-HT$_{2C}$ receptor is implicated and modulation of 5-HT$_{2C}$ function is desired, comprising administering a therapeutically effective amount of a compound of claim 19 to the mammal wherein the disease or condition is selected from the group consisting of anxiety, obesity, depression, panic disorder, a phobia and obsessive compulsive disorder.

58. A method for treating a disease or condition of the central nervous system in a mammal wherein the 5-HT$_{2c}$ receptor is implicated and modulation of 5-HT$_{2C}$ function is desired, comprising administering a therapeutically effective amount of a compound of claim 38 to the mammal wherein the disease or condition is selected from the group consisting of anxiety, obesity, depression, panic disorder, a phobia and obsessive compulsive disorder.

59. A method for treating disease or condition of the central nervous system in a mammal wherein the 5-HT$_{2c}$ receptor is implicated and modulation of 5-HT$_{2C}$ function is desired, comprising administering a therapeutically effective amount of a compound of claim 39 to the mammal, wherein the disease or condition is selected from the group consisting of anxiety, obesity, depression, panic disorder, a phobia and obsessive compulsive disorder.

* * * * *